United States Patent
Rughani et al.

(10) Patent No.: US 11,166,895 B2
(45) Date of Patent: Nov. 9, 2021

(54) HAIR CARE COMPOSITIONS COMPRISING THIOLACTIC ACID-BASED IONIC LIQUIDS OR THIOLACTIC ACID-BASED IONIC MIXTURES

(71) Applicant: L'OREAL, Paris (FR)

(72) Inventors: Ronak Rughani, Edison, NJ (US); Magali Moreau, Chatham, NJ (US); Julien Hitce, Aulnay-sous-Bois (FR); Maria Dalko, Versailles (FR); Alexandre Cavezza, Les Pavillons sous Bois (FR); Christian Blaise, Saint Mandé (FR); Robin D. Rogers, Montreal (CA); Giovanni Pietro Rachiero, Montreal (CA); Gabriela Gurau, Montreal (CA)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/331,568

(22) PCT Filed: Oct. 2, 2017

(86) PCT No.: PCT/IB2017/001416
§ 371 (c)(1),
(2) Date: Mar. 8, 2019

(87) PCT Pub. No.: WO2018/065827
PCT Pub. Date: Apr. 12, 2018

(65) Prior Publication Data
US 2019/0216705 A1     Jul. 18, 2019

Related U.S. Application Data

(60) Provisional application No. 62/403,481, filed on Oct. 3, 2016, provisional application No. 62/403,475, filed on Oct. 3, 2016.

(51) Int. Cl.
*A61K 8/46* (2006.01)
*A61K 8/41* (2006.01)
(Continued)

(52) U.S. Cl.
CPC .................. *A61K 8/46* (2013.01); *A61K 8/41* (2013.01); *A61K 8/416* (2013.01); *A61Q 5/02* (2013.01);
(Continued)

(58) Field of Classification Search
None
See application file for complete search history.

(56) References Cited

U.S. PATENT DOCUMENTS

| | | | |
|---|---|---|---|
| 3,157,578 A | 11/1964 | Zviak et al. | |
| 2013/0058852 A1* | 3/2013 | Atkins | B01D 53/1475 423/223 |

FOREIGN PATENT DOCUMENTS

| | | |
|---|---|---|
| CA | 2643784 A1 | 2/2009 |
| WO | 2010125302 A1 | 11/2010 |
| WO | 2013024099 A1 | 2/2013 |

OTHER PUBLICATIONS

English translation for WO 2010/125302 A1 (Description) (Year: 2010).*

(Continued)

Primary Examiner — Sin J Lee
(74) Attorney, Agent, or Firm — Polsinelli PC

(57) ABSTRACT

The instant disclosure relates hair care compositions comprising ionic liquids or ionic mixtures. Ionic liquids or ionic mixtures are combined with a cosmetically acceptable carrier to form ready-to-use hair care compositions. The ionic liquids and the ionic mixtures are formed from: (1) thiolactic acid and/or one or more alkali metal or alkaline earth metal salts thereof; and (2) one or more amine compounds, and/or (Continued)

one or more ammonium cationic compounds, and/or one or more salts thereof. The ionic liquids, the ionic mixtures, and the hair care compositions comprising the ionic liquids or the ionic mixtures, are useful in methods for preventing hair damage, shaping hair, caring for hair, etc.

9 Claims, 4 Drawing Sheets

(51) Int. Cl.
    *A61Q 5/02*        (2006.01)
    *A61Q 5/04*        (2006.01)
    *A61Q 5/06*        (2006.01)
    *A61Q 5/12*        (2006.01)

(52) U.S. Cl.
CPC ................ *A61Q 5/04* (2013.01); *A61Q 5/06* (2013.01); *A61Q 5/12* (2013.01); *A61K 2800/59* (2013.01); *A61K 2800/592* (2013.01); *A61K 2800/80* (2013.01); *A61K 2800/805* (2013.01)

(56) References Cited

OTHER PUBLICATIONS

English translation for WO 2010/125302 A1 (Claims) (Year: 2010).*
Compound Summary for 2-Mercaptopropionic acid—pages from PubChem website: https://pubchem.ncbi.nlm.nih.gov/compound/2-Mercaptopropionic-acid#section=Reactive-Group (an open chemistry database at the National Institutes of Health (date unknown).*
International Search Report and Written Opinion dated Feb. 14, 2018 for corresponding PCT Application No. PCT/IB2017/001416.

* cited by examiner

HAIR CARE COMPOSITIONS COMPRISING THIOLACTIC ACID-BASED IONIC LIQUIDS OR THIOLACTIC ACID-BASED IONIC MIXTURES

CROSS-REFERENCE TO RELATED APPLICATIONS

This application is a national stage application (under 35 U.S.C. § 371) of PCT/IB2017/001416, filed Oct. 2, 2017, which claims benefit of U.S. Provisional Application No. 62/403,481, filed Oct. 3, 2016, and U.S. Provisional Application No. 62/403,475, filed on Oct. 3, 2016, which are incorporated herein by reference in their entireties.

FIELD OF THE DISCLOSURE

The instant disclosure relates to thiolactic acid-based ionic liquids, thiolactic acid-based ionic mixtures, and the use of the ionic liquids or the ionic mixtures in hair care compositions for shaping or altering the shape of the hair, for example, by straightening or perming the hair. The disclosure further relates to methods of making the ionic liquids, methods of making the ionic mixtures, to hair care compositions comprising the ionic liquids or the ionic mixtures, and to methods for using the hair care compositions.

BACKGROUND

Cosmetic and personal care products for use on keratinous substrates such as hair are available commercially in various forms, for example, as creams, lotions, gels, pastes, and powders. Regardless of the form, these products have to achieve and provide certain benefits and attributes such as efficaciousness, cosmeticity, desirable texture, stable formulations, and ease and convenience of use and application. Thus, in order to meet changing consumer needs and preferences, manufacturers of such products continuously seek to re-formulate and create new products with enhanced efficacy, while still remaining stable and safe to use. In addition, manufacturers continue to test the use of new raw materials and ingredients or new product forms that would help deliver the desired attributes and properties with respect to viscosity, texture, stability and efficacy.

One area where manufacturers are always seeking to improve in is in the area of hair cosmetic products such as those products designed to change the appearance, shape or configuration of hair as well as to provide hair care benefits of manageability, frizz control, volume reduction, and improved quality of the hair fiber. Examples of such hair cosmetic products are hair relaxers or hair straighteners which can relax or straighten curly or kinky hair, including wavy hair. Other hair cosmetic products are perms and waving compositions for providing curl or shape to hair. These products may increase the manageability and ease of styling hair and they may either be applied in a hair salon by a professional or in the home by the individual consumer.

One type of composition that can be applied onto hair in order to change its shape and make it more manageable is an alkaline composition. Alkaline hair relaxing/straightening involves hydrolyzing the keratin of the hair with various alkaline agents, such as inorganic hydroxides, for instance sodium hydroxide, or organic hydroxides, such as guanidine hydroxide, or organic amines. Hair relaxing/straightening products that employ sodium hydroxide or potassium hydroxide are also called lye-based products and products that use other alkaline agents such as lithium hydroxide, calcium hydroxide, organic hydroxides and other non-hydroxide compounds, for example, organic amines, generally fall under the category of no-lye products.

Still, it is desirable to find alternatives to the alkaline lye- and no-lye-based products and process described above which can damage the hair by weakening and/or causing dryness of the hair fibers. However, the discovery of new compositions and processes for changing the shape of hair that impart less or minimal damage to hair, may pose challenges to manufacturers and formulators because the incorporation of new ingredients into the compositions may negatively impacting their performance, cosmetic attributes, and formulation stability. In addition, the alkalinity and/or pH is an important consideration for these products. New processes for treating and changing the shape of hair may also impact the performance of the compositions, processing times and quality of use.

SUMMARY OF THE DISCLOSURE

The instant disclosure relates to the use of thiolactic acid based ionic liquids or thiolactic acid-based ionic mixtures in the treatment of hair. The inventors discovered that thiolactic acidbased ionic liquids or thiolactice acid-based ionic mixtures can be used in hair care compositions for shaping or altering the shape of hair, e.g., perming or straightening the hair, for example using heat. Additionally, the ionic liquids or ionic mixtures can be used to impart hair care benefits to the hair, such as manageability, frizz control, and volume reduction. Hair care compositions comprising the ionic liquids or the ionic mixtures are unique because they eliminate or greatly reduce damage to the hair. Ionic liquids are additionally unique because they eliminate or greatly reduce the objectionable odor associated with thiolactic acid and its salts. Thiolactic acid is typically provided as a liquid and is known to have a distinct unpleasant odor. While not wishing to be bound by any particular theory, the inventors believe that the association formed between oppositely charged components allows for hair care compositions comprising the ionic liquids or the ionic mixtures to effectively treat the hair (e.g., alter the shape of the hair) without damaging the hair (or by reducing damage to hair). Ionic liquids simultaneously reduce or eliminate the objectionable odor of the thiolactic acid and/or its salts.

With respect to ionic liquids, a typical hair care composition according to the instant disclosure comprises: (a) an ionic liquid, the ionic liquid comprising thiolactate anion and one or more ammonium cationic compounds and (b) a cosmetically acceptable carrier. In some cases, the hair care composition has a pH of about 3 to about 10, about 3 to about 8, about 3 to about 7, or about 4 to about 6. The amount of the thiolactate anion and the amount of the one or more ammonium cationic compounds (cation) of the ionic liquid can vary provided that they these components associate with each other to form an ionic liquid. In some cases, the molar ratio of the total amount of the thiolactate anion to the total amount of the ammonium cationic compounds (cation) in the ionic liquid is about 1:1.

With respect to ionic mixtures, a typical hair care composition according to the instant disclosure comprises: (a) an ionic mixture comprising thiolactic acid and/or one or more alkali metal or alkaline earth metal salts thereof, and one or more amine compounds, and/or one or more ammonium cationic compounds, and/or one or more salts thereof; (b) optionally, one or more neutralizing agents, wherein the neutralizing agent is different from the one or more amine compounds and/or one or more ammonium cationic compounds and/or one or more salts thereof in (a); and (c) a cosmetically acceptable carrier. In some cases, the hair care composition has a pH of about 3 to about 10, about 3 to about 8, about 3 to about 7, or about 4 to about 6.

The total amount of the thiolactic acid and/or one or more alkali metal and/or alkaline earth metal salts thereof and the total amount of the one or more amine compounds, and/or one or more ammonium cationic compounds, and/or one or more salts thereof in the ionic mixture, can vary. For example, in some cases, the molar ratio of the total amount of the thiolactic acid and/or one or more alkali metal and/or alkaline earth metal salts thereof to the total amount of the one or more amine compounds, and/or one or more ammonium cationic compounds, and/or one or more salts thereof, in the ionic mixture is about 10:1 to about 1:10.

The instant disclosure further relates to methods for making and using the hair care compositions described herein and to hair care compositions made according to the methods described herein.

Typically, an ionic liquid is formed and then the ionic liquid is subsequently added to a hair care composition, thereby creating a ready-to-use hair care composition that can immediately be applied to hair. For example, an ionic liquid can be formed by: (i) cooling one or more amine compounds and/or one or more ammonium cationic compounds and/or one or more salts thereof to a temperature below 15° C.; (ii) adding thiolactic acid and/or one or more alkali metal and/or alkaline earth metal salts thereof to the cooled one or more amine compounds and/or one or more ammonium cationic compounds and/or one or more salts thereof; (iii) removing water and optionally removing resulting metal salts; and (iv) obtaining the ionic liquid in the form of a viscous oil. After forming the ionic liquid it can be immediately added to a cosmetically acceptable carrier to form a hair care composition or it can be stored for later use. Three different generic synthesis schemes for forming ionic liquids shown below:

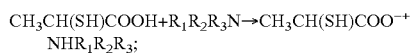  1)

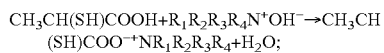  2)

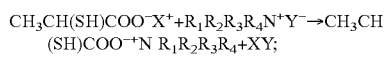  3)

wherein X is an alkali metal or alkali earth metal, Y is a halide anion;

$CH_3CH(SH)COOH$ is thiolactic acid and $CH_3CH(SH)COO^-X^+$ is a thiolactic acid salt of an alkali metal and/or alkaline earth metal; and $R^1$, $R^2$, $R^3$ and $R^4$ are independently hydrogen, phenyl, benzyl, a saturated, branched or unbranched alkyl residue with a chain length of 1 to 30 carbon atoms, which may optionally be substituted with one or more hydroxyl groups, thiol groups, carboxylic groups and/or aryl groups, wherein the alkyl residue with a chain length of 8 to 30 carbon atoms may be interrupted by one or more oxygen atoms, sulfur atoms, and/or NR groups, wherein R is hydrogen or a saturated, branched or unbranched alkyl residue with a chain length 1 to 6; and wherein at least one of $R^1$, $R^2$, $R^3$ and $R^4$ is not hydrogen.

More specific, non-limiting exemplary synthesis schemes for producing ionic liquids are presented below.

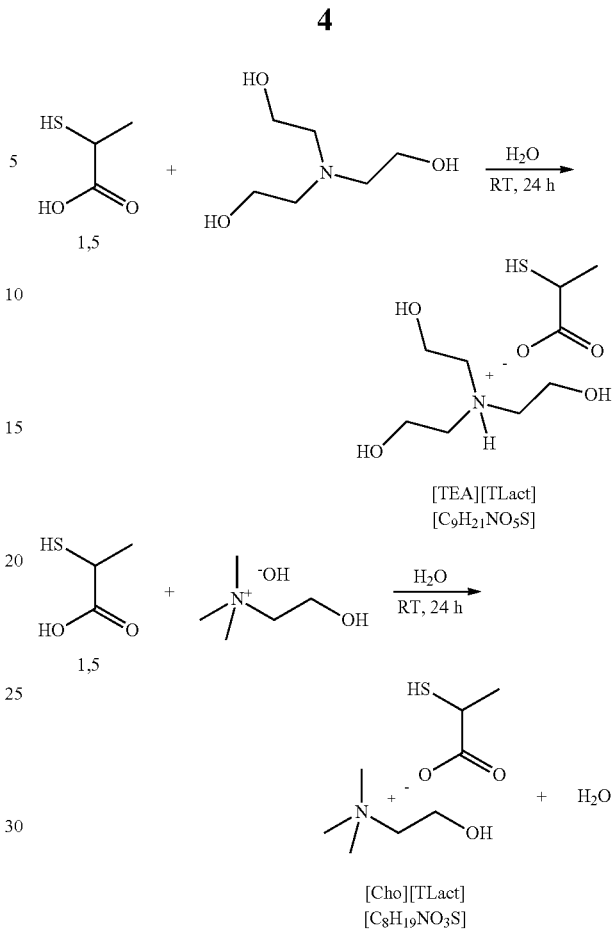

An ionic mixture is formed, for example, by mixing thiolactic acid and/or one or more alkali metal or alkaline earth metal salts thereof with one or more amine 10 compounds and/or one or more ammonium cationic compounds and/or one or more salts thereof. After mixing the thiolactic acid and/or one or more alkali metal or alkaline earth metal salts thereof with the one or more amine compounds and/or one or more ammonium cationic compounds and/or one or more salts thereof, additional processing is typically not required to form the ionic mixtures. For example, removal of water and/or resulting metal salts from the combination is not required. After forming the ionic mixture it can be immediately added to a cosmetically acceptable carrier to form a hair care composition or it can be stored for later use. No post processing is required.

In some instances, the ionic liquid or the ionic mixture is stored for later use and can be individually packaged in order to isolate the ionic liquid or the ionic mixture from other components of a hair care composition. For examples, the ionic liquid or the ionic mixture may be stored in a separate bottle, ampoule, syringe, etc. The separately packaged ionic liquid or ionic mixture can be part of a kit. Such kits include, for example, an ionic liquid or ionic mixture, and separately, a cosmetically acceptable carrier. For example, the cosmetically acceptable carrier to which an ionic liquid or ionic mixture is combined could be a shampoo, a conditioner, etc. The ionic liquid or ionic mixture can be combined with the cosmetically acceptable carrier to generate a ready-to-use hair care composition for immediate application to hair. Typically, the ready-to-use hair care composition is applied to the hair within 30 minutes after mixing the ionic liquid or the ionic mixture with the cosmetically acceptable carrier (e.g., within 30 minutes of mixing the ionic liquid or ionic mixture with a shampoo, a conditioner, etc.)

The instant disclosure relates to methods of treating hair with the ionic liquids or the ionic mixture and to hair care compositions comprising the ionic liquids or the ionic mixtures. For example, if the ionic liquid or the ionic mixture is already incorporated into a hair care composition, a method for shaping hair or altering the shape of hair or for caring for the hair may include: (1) applying a hair care composition comprising the ionic liquid or the ionic mixture to hair; (2) optionally, brushing, combing, or smoothing the hair; (3) optionally, rinsing the hair; (4) heating the hair at to temperature of at least 25° C., 30° C., 35° C., 40° C., 45° C., or 50° C. while optionally applying a smoothing action (or other shaping action) to the hair; and (5) optionally, rinsing the hair with water. The method may additionally include contacting the hair after (2) with a shampoo and/or a conditioner, followed by rinsing with water. If the ionic liquid or ionic mixture is stored separately, for example, as part of a kit, the method may further include forming a ready-to-use hair care composition by adding the ionic liquid or ionic mixture to a cosmetically acceptable carrier to form a ready-to-use hair care composition that can subsequently be used to treat hair, as described above.

The ionic liquids and the ionic mixtures, and the hair care compositions comprising the ionic liquids or the ionic mixtures, are unique in their ability to preserve hair fiber integrity, such that hair fibers treated with the ionic liquids or the ionic mixtures, or the hair care compositions comprising the ionic liquids or the ionic mixtures, have hair fiber integrity and properties very similar to that of natural hair. This is because the ionic liquids and ionic mixtures are gentle to the hair and cause little if any damage to the hair fibers (and appear to provide protective properties to the hair fibers). Accordingly, the ionic liquids and ionic mixtures and the hair care compositions comprising them are useful in methods for preserving hair fiber integrity, such that the hair fiber integrity remains similar or substantially identical to natural hair. The methods include treating the hair with the ionic liquids, the ionic mixtures, or the hair care compositions comprising the ionic liquids or the ionic mixtures.

As mentioned previously, the ionic liquids, and the hair care compositions comprising the ionic liquids, have little or no objectionable odor. Thiolactic acid and its salts are known to have a distinct unpleasant odor. Surprisingly, when thiolactic acid and/or its salts are incorporated into an ionic liquid, which can be further incorporated into a hair care composition, the objectionable odor associated with the thiolactic acid and/or its salts is eliminated or reduced. Thus, the ionic liquids and the hair care compositions comprising the ionic liquids are not only effective and gentle, but additionally do not exhibit an objectionable odor. Accordingly, the instant disclosure relates to methods for reducing odor of a hair care composition, the method comprising forming an ionic liquid, and adding the ionic liquid to a hair care composition.

Finally, the instant disclosure relates to methods of treating hair using the ionic liquids, the ionic mixtures, or hair care compositions comprising the ionic liquids or the ionic mixtures. For example, the instant disclosure relates to methods for imparting to the hair one or more of straightening effects; manageability; frizz control; volume reduction or volume control; styling effects; curling effects; relaxing effects; improvement or retention of curl definition; humidity resistance; and/or improvement of the appearance of hair.

BRIEF DESCRIPTION OF THE DRAWINGS

Implementations of the present technology will now be described, by way of example only, with reference to the attached figures, wherein.

Figure 1:
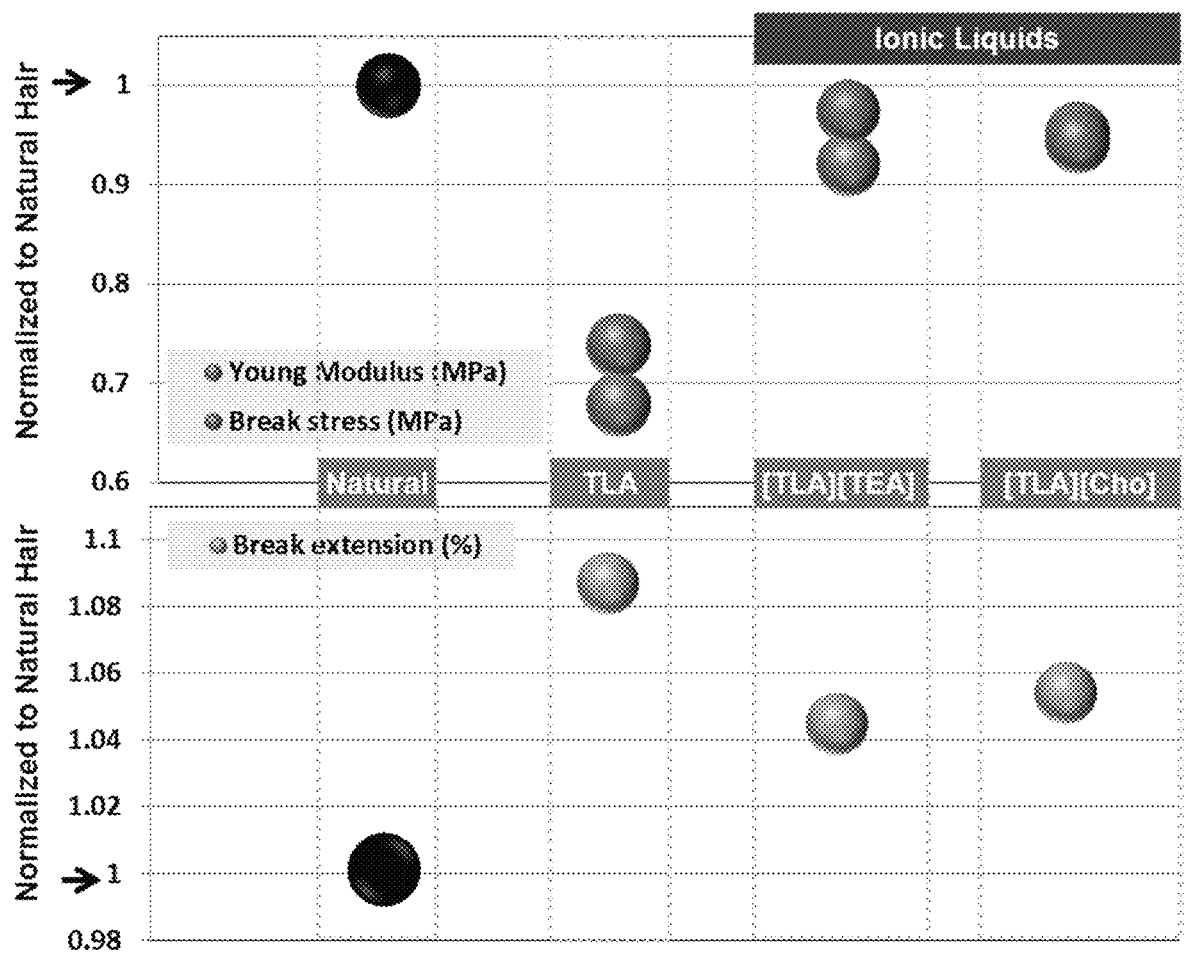
FIG. 1 is a graph showing the Young's Modulus, the break test results, and the break extension (%) for natural hair, hair treated with thiolactic acid (TLA), and hair treated with thiolactic acid-based ionic liquids.

It should be understood that the various aspects are not limited to the arrangements and instrumentality shown in the drawings.

DETAILED DESCRIPTION OF THE DISCLOSURE

The instant disclosure relates generally to thiolactic acid-based ionic liquids, thiolactic acid-based ionic mixtures, and to hair care compositions comprising the ionic liquids or the ionic mixtures.

Ionic Liquids

With respect to ionic liquids, a typical hair care compositions according to the instant disclosure comprises: (a) an ionic liquid, wherein the ionic liquid comprises thiolactate anion and one or more ammonium cationic compounds, and (b) a cosmetically acceptable carrier. The pH of the hair care composition may be from about 3 to about 10, about 3 to about 8, from about 3 to about 7, from about 3 to about 6, from about 3 to about 5, from about 4 to about 7, from about 4 to about 6, from about 4 to about 5, or from about 5 to about 6.

The molar ratio of the thiolactate anion to the one or more ammonium cationic compounds (cation) (in monomeric or polymeric form) in the ionic liquid is about 1:1. The molar ratio is about 1:1 because the thiolactate anion forms an ionic interaction or association with an ammonium cation of the one or more amine compounds and/or one or more ammonium cationic compounds and/or the salts thereof. The ionic interaction or association typically results in ionic bonds forming between the oppositely charged components of the ionic liquids, which are usually stronger than the Van der Waals forces between the molecules of ordinary liquids. In some cases, the thiolactic acid and/or one or more alkali or alkaline earth metal salts thereof, used to form the ionic liquid is selected from the group consisting of thiolactic acid, sodium thiolactic acid (sodium thiolactate), potassium thiolactic acid (potassium thiolactate), magnesium thiolactic acid (magnesium thiolactate), strontium thiolactic acid (strontium thiolactate), and mixtures thereof.

One or more amine compounds and/or one or more ammonium cationic compounds and/or one or more salts thereof, can be combined with the thiolactic acid and/or one or more alkali metal and/or alkaline earth metal salts thereof to form the ionic liquid. The one or more amine compounds become cationic when neutralized, for example, with an acid that forms the anionic part of the ionic liquid. Non-limiting examples of useful amines for forming an ionic liquid include N,N,N-trimethylhydroxyethylammonium chloride (choline chloride), choline hydroxide, triethanolamine, monethanolamine, and mixtures thereof. Additionally, in some cases, the one or more ammonium cationic compounds used to form the ionic liquid include one or more compounds and/or salts of formula (I):

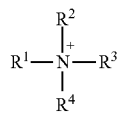

Formula (I)

in which $R^1$, $R^2$, $R^3$ and $R^4$ are independently hydrogen, phenyl, benzyl, a saturated, branched or unbranched alkyl residue with a chain length of 1 to 30 carbon atoms, which may optionally be substituted with one or more hydroxyl groups, thiol groups, carboxylic groups, and/or aryl groups, wherein the alkyl residue with a chain length of 1 to 30 carbon atoms may be interrupted by one or more oxygen atoms, sulfur atoms, and/or NR groups, wherein R is hydrogen or a saturated, branched or unbranched alkyl residue with a chain length 1 to 6; and wherein at least one of $R^1$, $R^2$, $R^3$ and $R^4$ is not hydrogen.

The one or more ammonium cationic compounds and/or salts thereof may include one or more compounds and/or salts of formula (I) (above), wherein $R^1$, $R^2$, $R^3$ and $R^4$ are independently hydrogen or a saturated, branched or unbranched alkyl residue with a chain length of 1 to 10 carbon atoms, which may optionally be substituted with one or more hydroxyl groups, thiol groups, carboxylic groups, and/or aryl groups, wherein the alkyl residue with a chain length of 1 to 10 carbon atoms may be interrupted by one or more oxygen atoms, sulfur atoms, and/or NR groups, wherein R is hydrogen or a saturated, branched or unbranched alkyl residue with a chain length 1 to 6; and wherein at least one of $R^1$, $R^2$, $R^3$ and $R^4$ is not hydrogen.

The one or more ammonium cationic compounds and/or salts thereof may include one or more compounds and/or salts of formula (I) (above), wherein $R^1$, $R^2$, $R^3$ and $R^4$ are independently hydrogen or a saturated, branched or unbranched alkyl residue with a chain length of 1 to 10 carbon atoms, which may optionally be substituted with one or more hydroxyl groups, carboxylic groups, or thiol groups, wherein the alkyl residue with a chain length of 1 to 10 carbon atoms may be interrupted by one or more oxygen atoms or sulfur atoms; and wherein at least one of $R^1$, $R^2$, $R^3$ and $R^4$ is not hydrogen.

Additionally, the one or more ammonium cationic compounds and/or salts thereof may be a cationic imidazolium compound of formula (II)

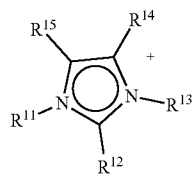

Formula II wherein $R^{11}$ and $R^{13}$ are the same or different and are each selected from the group consisting of an alkyl group of 1 to 10 or 1 to 6 carbon atoms, a cycloalkyl group of 4 to 10 carbon atoms, an aryl group of 6 to 10 carbon atoms, and a tri(C1-C10)alkylsilyl group, $R^{12}$ is selected from the group consisting of hydrogen, an alkyl group of 1 to 10 or 1 to 6 carbon atoms, a cycloalkyl group of 4 to 10 carbon atoms, an aryl group of 6 to 10 carbon atoms and a halogen atom; in some cases, $R^{12}$ is an alkyl group, a cycloalkyl group or an aryl group as defined above, $R^{14}$ and $R^{15}$ are the same or different and are each selected from the group consisting of hydrogen, an alkyl group of 1 to 10 or 1 to 6 carbon atoms, a cycloalkyl group of 4 to 10 carbon atoms, an aryl group of 6 to 10 carbon atoms, a tri(C1-C10)alkylsilyl group, and a halogen atom; in some cases $R^{14}$ and $R^{15}$ are the same or different and are hydrogen, an alkyl group, a cycloalkyl group, an aryl group, or a tri(C1-C10)alkylsilyl group; in some cases $R^{14}$ and $R^{15}$ are hydrogen.

The aforementioned alkyl group having 1 to 10 carbon atoms (sometimes abbreviated as "C1-C10"), or 1 to 6 carbon atoms (sometimes abbreviated as "C1-C6") in the definitions of $R^1$ to $R^{15}$ include optionally substituted linear or branched alkyl groups, such as methyl, ethyl, n-propyl, isopropyl, n-butyl, iso-butyl, sec-butyl, tert-butyl, n-pentyl, iso-pentyl, neo-pentyl, n-hexyl, n-heptyl, n-octyl, n-nonyl and n-decyl. Alkyl groups may be substituted by one or more substituents, identical or different. Among these substituents are halogen atoms. In some cases, alkyl groups with 1 to 6-carbon atoms are used, e.g. methyl, ethyl, propyl, iso-propyl, butyl, sec-butyl, iso-butyl, tert-butyl, 1-pentyl, 2-pentyl, 3-pentyl, iso-amyl, n-hexyl and iso-hexyl. In some cases, preferred substituted alkyl groups are haloalkly and perhaloalkyl, e.g. trifluoromethyl, 1,1,1-trifluoroethyl, perfluoroethyl, perfluoropropyl, 1,1,1,2,2,3,3-heptafluorobutyl and perfluorobutyl.

The aforementioned cycloalkyl group of 6 to 10 carbon atoms includes for example cyclobutyl, cyclopentyl, cyclohexyl, cycloheptyl, and cyclo-octyl, as well as bicycloalkyl groups, e.g. bicyclo[3.3.0]octyl, bicyclo[4.3.0]nonyl, bicyclo[4.4.0]decyl and bicyclo[2.2.1]heptyl. Tricycloakyl groups, for example adamantyl, are included in the definition of cycloalkyl. Cycloalkyl groups may be substituted by one or more identical or different substituents chosen, for example, from among alkyl groups and halogen atoms.

The aforementioned aryl group of 6 to 10 carbon atoms includes for example phenyl or naphthyl. Aryl groups may bear one or more substituents, identical or different.

With respect to the above mentioned (C1-C6) alkyl moiety of the tri(C1-C6)alkylsilyl group it is referred to the definition of the (C1-C6)alkyl groups for $R^{11}$ to $R^{15}$.

Halogen atoms in the above definitions include for example fluorine, chlorine, bromine and iodide.

With respect to the aforementioned (C1-C10)alkyl moiety in the definitions "bis-perfluoro(C1-C10)alkylsulphonyl amide" and "perfluoro(C1-C10)alkyl sulphonate" it is referred to the definition of the C1-C10 alkyl groups for $R^{11}$ to $R^{15}$ above.

In some instances, preferred imidazolium compounds of formula (II) are those having the following characteristics taken alone or in combination: $R^{11}$, $R^{12}$ and $R^{13}$, identical or different, are each independently chosen from (C1-C6)alkyl, (C1-C6)haloalkyl and cycloalkyl; $R^{14}$ and $R^{15}$, identical or different, are each independently chosen from hydrogen, (C1-C6)alkyl, (C1-C6)haloalkyl and cycloalkyl.

In some cases, preferred imidazolium compounds of formula (II) have the following characteristics taken alone or in combination: $R^{11}$, $R^{12}$ and $R^{13}$, identical or different, are each independently chosen from methyl, ethyl, propyl, iso-propyl, butyl, sec-butyl, 1-pentyl, 2-pentyl, 3-pentyl, iso-pentyl, hexyl, iso-hexyl, cyclohexyl, trifluoromethyl, 1,1,1-trifluoroethyl, perfluoroethyl, perfluoropropyl, 1,1,1,2,2,3,3-heptafluorobutyl, and perfluorobutyl; $R^{14}$ and $R^{15}$, identical or different, are each independently chosen from hydrogen, methyl, ethyl, propyl, iso-propyl, butyl, sec-butyl, 1-pentyl, 2-pentyl, 3-pentyl, iso-pentyl, hexyl, iso-hexyl, cyclohexyl, trifluoromethyl, 1,1,1-trifluoroethyl, perfluoroethyl, perfluoropropyl, 1,1,1,2,2,3,3-heptafluorobutyl, and perfluorobutyl.

In some cases, the compound(s) of formula (II) are 1,2,3-tri(C1-C10)alkyl-imidazolium salts. With respect to the aforementioned (C1-C10) alkyl moiety in the "1,2,3-tri(C1-C10)-alkyl-imidazolium salts" it is referred to the definition of the C1-C10 alkyl groups for $R^1$ to $R^{15}$ above.

In some cases, the compounds of formula (II) include 1-ethyl-2,3-dimethylimidazolium bromide ([EMMI][Br]), 1-ethyl-2,3-dimethylimidazolium bistrifluoromethylsulphonylamide ([EMMI][Tf$_2$N]), 1-ethyl-2,3-dimethylimidazolium trifluoromethylsulphonate ([EMMI][CF$_3$SO$_3$]), 1-n-butyl-2,3-dimethylimidazolium chloride ([BMMI][Cl]), 1-n-butyl-2,3-dimethylimidazolium hexafluorophosphate ([BMMI][PF$_6$]), 1-n-butyl-2,3-dimethylimidazolium bistrifluoromethylsulphonylamide ([BMMI][Tf$_2$N]), and 1-n-butyl-2,3-methylimidazolium tetrafluoroborate ([BMMI][BF$_4$]).

In some cases 1-n-butyl-2,3-dimethylimidazolium salt is used, and more specifically 1-n-butyl-2,3-dimethylimidazolium chloride, 1-n-butyl-2,3-dimethylimidazolium hexafluorophosphate, 1-n-butyl-2,3-dimethylimidazolium bistrifluoromethylsulphonylamide and/or 1-n-butyl-2,3-methylimidazolium tetrafluoroborate.

Furthermore, in some instances, the one or more ammonium cationic compounds and/or salts thereof may be a cationic imidazolium compound of formula (III)

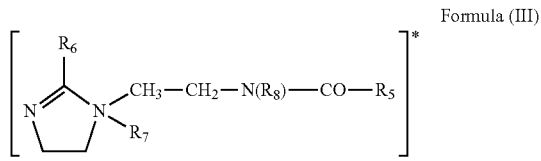

Formula (III)

wherein $R_5$ and $R_6$ are chosen from alkenyl and alkyl radicals comprising from 1 to 30 carbon atoms or alkenyl and alkyl radicals derived from palm oil or hydrogenated tallow; $R_6$ is chosen from hydrogen, C1-C4 alkyl radicals, and alkenyl and alkyl radicals comprising from 8 to 30 carbon atoms; $R_7$ is chosen from C1-C4 alkyl radicals; and $R_8$ is chosen from hydrogen and C1-C4 alkyl radicals. If an anion is present, it may be chosen from, for example, halides, phosphates, acetates, lactates, alkyl sulfates, alkyl sulfonates, and alkylaryl sulfonates. Non-limiting examples of cationic imidazolium compounds of formula (III) include quaternium-83, quaternium-87, and mixtures thereof.

Furthermore, in some instances, the one or more ammonium cationic compounds and/or salts thereof may be polyammonium cationic compounds (two or more ammonium groups) such as diammonium and triammonium cationic compounds. Such compounds may be organic acid salts such as diammonium citrate or inorganic salts such as diammonium phosphate or diammonium sulfate.

Additionally, in some cases, the one or more amine compounds used to form the ionic liquid include alkyl amine compounds, alkylene amine compounds, and mixtures thereof. In some cases, the alkyl or alkylene group is from 2 to 4 carbon atoms. In yet other cases, the amine compounds are chosen from monoamine and polyamine compounds. The one or more amine compounds used to form the ionic liquids become cationic when neutralized, for example, with an acid that forms the anion part of the ionic liquid. In other words, the one or more amine compounds become one or more cationic ammonium compounds at the appropriate pH. Thus, an ionic liquid can be formed from thiolactic acid and/or one ore more alkali metal and/or alkaline earth metal salts thereof and one or more amine compounds. In the ionic liquid, the one or more amine compounds therefore become one or more cationic ammonium compounds (cation).

More specifically, the one or more amine compounds and/or the one or more ammonium cationic compounds and/or salts thereof may be selected from the group consisting of a betaine (trimethylglycine or 1-Carboxy-N,N,N-Trimethylmethanaminium Hydroxide, Inner Salt), carnitine (Ammonium, (3-carboxy-2-hydroxypropyl)trimethyl-, hydroxide, inner salt, L-), choline salt (N,N,N-trimethylhydroxyethylammonium or 2-Hydroxy-N,N,N-trimethylethan-1-aminium salt) tris-(2-hydroxyethyl) methylammonium salt, tetramethylammonium salt, tetraethylammonium salt, diethyldimethylammonium salt, bis-(2-hydroxyethyl) dimethylammonium salt, tetrabutylammonium salt, tetrapropylammonium salt, triethanolamine (TEA), monoethanolamine (MEA), and mixtures thereof.

The salts of the one or more ammonium cationic compounds of the present invention are alkali metal or alkaline earth metal salts or salts of organic acids.

The one or more ammonium cationic compounds of the present invention may also be hydroxide compounds.

Various amounts of ionic liquids can be added to cosmetically acceptable carriers to form hair care compositions. The ionic liquid is roughly about half thiolactate anion and about half ammonium cation (about a 1:1 molar ratio). In some cases, the ionic liquid can be added to a cosmetically acceptable carrier such that about half of the hair care composition comprises the ionic liquid. Thus, in some cases, about 1 wt. % to about 50 wt. % of ionic liquid is combined with a cosmetically acceptable carrier to form a hair care compositions, wherein the weight percentages are based on the total weight of the hair care composition. Likewise, about 1 wt. % to about 45 wt. %, about 1 wt. % to about 40 wt. %, about 1 wt. % to about 35 wt. %, about 1 wt. % to about 30 wt. %, about 1 wt. % to about 25 wt. %, about 1 wt. % to about 20 wt. %, about 1 wt. % to about 15 wt. %, or about 1 wt. % to about 10 wt. % of ionic liquid is combined with a cosmetically acceptable carrier to form a hair care compositions, wherein the weight percentages are based on the total weight of the hair care composition. Furthermore, about 2 wt. % to about 45 wt. %, about 2 wt. % to about 40 wt. %, about 2 wt. % to about 35 wt. %, about 2 wt. % to about 30 wt. %, about 2 wt. % to about 25 wt. %, about 2 wt. % to about 20 wt. %, about 2 wt. % to about 15 wt. %, or about 2 wt. % to about 10 wt. % of ionic liquid is combined with a cosmetically acceptable carrier to form a hair care compositions, wherein the weight percentages are based on the total weight of the hair care composition. Additionally, about 3 wt. % to about 45 wt. %, about 3 wt. % to about 40 wt. %, about 3 wt. % to about 35 wt. %, about 3 wt. % to about 30 wt. %, about 3 wt. % to about 25 wt. %, about 3 wt. % to about 20 wt. %, about 3 wt. % to about 15 wt. %, or about 3 wt. % to about 10 wt. % of ionic liquid is combined with a cosmetically acceptable carrier to form a hair care compositions, wherein the weight percentages are based on the total weight of the hair care composition.

The hair care compositions of the instant disclosure typically include about 1 wt. % to about 25 wt. % of the thiolactate and a total amount of about 1 wt. % to about 25 wt. % of the one or more ammonium cationic compounds. The total amount of the thiolactate in the hair care compositions may be about 1 wt. % to about 20 wt. %, about 1 wt. % to about 15 wt. %, about 1 wt. % to about 12 wt. %, about 1 wt. % to about 10 wt. %, or about 1 wt. % to about 8 wt. %. Likewise, the total amount of the thiolactate in the hair care compositions may be about 2 wt. % to about 25 wt. %, about 2 wt. % to about 20 wt. %, about 2 wt. % to about 15 wt. %, about 2 wt. % to about 12 wt. %, about 2 wt. % to about 10 wt. %, or about 2 wt. % to about 8 wt. %. Furthermore, the total amount of the thiolactate in the hair care compositions may be about 3 wt. % to about 25 wt. %, about 3 wt. % to about 20 wt. %, about 3 wt. % to about 15 wt. %, about 3 wt. % to about 12 wt. %, about 3 wt. % to about 10 wt. %, or about 3 wt. % to about 8 wt. %.

The total amount of the one or more ammonium cationic compounds in the hair care compositions may be about 1 wt. % to about 20 wt. %, about 1 wt. % to about 15 wt. %, about 1 wt. % to about 12 wt. %, about 1 wt. % to about 10 wt. %, or about 1 wt. % to about 8 wt. %. Likewise, the total amount of the one or more ammonium cationic compounds in the hair care compositions may be about 2 wt. % to about 25 wt. %, about 2 wt. % to about 20 wt. %, about 2 wt. % to about 15 wt. %, about 2 wt. % to about 12 wt. %, about 2 wt. % to about 10 wt. %, or about 2 wt. % to about 8 wt. %. Furthermore, the total amount of the one or more ammonium cationic in the hair care compositions may be about 3 wt. % to about 25 wt. %, about 3 wt. % to about 20 wt. %, about 3 wt. % to about 15 wt. %, about 3 wt. % to about 12 wt. %, about 3 wt. % to about 10 wt. %, or about 3 wt. % to about 8 wt. %.

The hair care compositions of the instant disclosure include an ionic liquid, which is typically combined with a cosmetically acceptable carrier. The combination of the ionic liquid and the cosmetically acceptable carrier typically results in a ready-to-use hair care compositions. The hair care compositions may be pre-mixed and sold as a single ready-to-use product, or may be supplied in the form of a kit, wherein the ionic liquid is separated from the cosmetically acceptable carrier, and the ionic liquid and the cosmetically acceptable carrier are mixed immediately before application to the hair to form a ready-to-use hair care composition. For example, the ionic liquid may be added and mixed to the cosmetically acceptable carrier and applied to the hair within about 30 min., about 20 min., about 15 min., about 10 min., or about 5 min.

In some instances, the cosmetically acceptable carrier is anhydrous or essentially anhydrous. The term "essentially anhydrous" indicates that the composition contains about 5 wt. % of less of water. In some cases, the anhydrous cosmetically acceptable carrier comprises about 4 wt. %, about 3 wt. %, about 2 wt. %, or about 1 wt. % or less of water. The total amount of the anhydrous cosmetically acceptable carrier may be 50 to 96 wt. %, based on the total weight of the hair care composition. Further, the total amount of the anhydrous cosmetically acceptable carrier may be about 50 to about 95 wt. %, about 50 to about 92 wt. %, about 50 to about 90 wt. %, about 50 to about 85 wt. %, about 50 to about 80 wt. %, 55 to about 95 wt. %, about 55 to about 92 wt. %, about 55 to about 90 wt. %, about 55 to about 85 wt. %, about 55 to about 80 wt. %, about 60 to about 95 wt. %, about 60 to about 92 wt. %, about 60 to about 90 wt. %, about 60 to about 85 wt. %, about 60 to about 80 wt. %.

Anhydrous component useful as part of the anhydrous cosmetically acceptable carrier include, for example, liquid polyols such as polyethylene glycol, propylene glycol, butylene glycol, hexylene glycol, glycerin, diglycerin, diethylene glycol, dipropylene glycol, and mixtures thereof; liquid paraffin; mineral oil; vegetable oil; ester oils such as pentaerythritol ester oils, trimethylol ester oils, citrate ester oils, glyceryl ester oils, and mixtures thereof. The polyethylene glycols useful herein are those having the formula:

$$H(OCH_2CH_2)_n\text{—}OH$$

wherein n has an average value of from 4 to 12. The polyethylene glycol described above is also known as a polyethylene oxide, and polyoxyethylene. Polyethylene glycols useful herein include PEG-200 wherein n has an average value of about 4.

The cosmetically acceptable carrier may also be aqueous. In addition to water, the aqueous carrier may include water soluble components, such as glycerin, $C_{1-4}$ alcohols, organic solvents, polyols, glycols, and combinations thereof. The total amount of the aqueous cosmetically acceptable carrier may be 50 to 96 wt. %, based on the total weight of the hair care composition. Further, the total amount of the cosmetically acceptable carrier may be about 50 to about 95 wt. %, about 50 to about 92 wt. %, about 50 to about 90 wt. %, about 50 to about 85 wt. %, about 50 to about 80 wt. %, 55 to about 95 wt. %, about 55 to about 92 wt. %, about 55 to about 90 wt. %, about 55 to about 85 wt. %, about 55 to about 80 wt. %, about 60 to about 95 wt. %, about 60 to about 92 wt. %, about 60 to about 90 wt. %, about 60 to about 85 wt. %, or about 60 to about 80 wt. %.

In some instances, the hair care composition of the instant disclosure is in the form of an emulsion, for example, oil in water emulsion (O/W emulsion) or water in oil (W/O emulsion). When the hair care composition is in the form of an emulsion, both an aqueous cosmetically acceptable carrier and an anhydrous cosmetically acceptable carrier exist. In other words, the hair care composition includes an aqueous phase and a fatty phase. Typically, the ionic liquids will be added to anhydrous phase (or the fatty phase) of the emulsion.

The hair care compositions of the instant disclosure may be in the form of a gel or a cream and independently may have a viscosity of about 405 to about 450 cps or mPa·s), which corresponded to a texture and consistency of some gels. The gel texture provides the benefits of ease of application of the composition into the hair, spreadability of the composition on the hair, and/or ease of brushing or combing the hair. A hair care composition in the form of a gel or a cream does not readily drip off from the hair; the gel or cream remains adhered to the hair during processing with the hair care composition.

The instant disclosure relates to methods for making ionic liquids and hair care compositions comprising ionic liquids. For example, methods for making hair care compositions according to the instant disclosure include forming an ionic liquid and combining the ionic liquid with a cosmetically acceptable carrier, wherein forming the ionic liquid comprises: (i) cooling one or more amine compounds and/or one or more ammonium cationic compounds and/or one or more salts thereof to a temperature below 15° C.; (ii) adding thiolactic acid and/or one or more alkali metal and/or alkaline earth metal salts thereof to the cooled one or more amine compounds and/or one or more ammonium cationic compounds and/or one or more salts thereof; (iii) removing water and optionally removing resulting metal salts; and (iv) obtaining the ionic liquid in the form of a viscous oil. In some cases, the one or more amine compounds and/or one or more ammonium cationic compounds and/or one or more salts thereof of (i) are cooled to a temperature of about 14° C. or less, about 13° C. or less, about 12° C. or less, about 10° C. or less, about 5° C. or less, or about 00° C. or less. Furthermore, the water in (iii) can be removed by various methods known in the art. In some cases, the water may be removed by rotatory evaporation and the residue washed with an organic solvent, such as diethylether.

In addition to methods for making the hair care compositions, as described above, the instant disclosure also relates to hair care compositions made by the methods. For examples, hair care compositions manufactured by forming an ionic liquid and combining the ionic liquid with a cosmetically acceptable carrier, wherein forming the ionic liquid is described above.

The ionic liquids and the hair care compositions comprising the ionic liquids are useful for shaping hair, altering the shape of hair, and for caring for the hair. Accordingly, the instant disclosure is directed to methods for shaping hair, altering the shape of hair, and for caring for the hair, the methods comprising: (1) applying a hair care composition as described herein to hair; (2) optionally, brushing, combing, or smoothing the hair; (3) optionally, rinsing the hair; (4) heating the hair at to temperature of at least 25° C., 30° C., 35° C., 40° C., 45° C., or 50° C., while optionally applying a smoothing action to the hair; and (5) optionally, rinsing the hair with water. The methods an further comprise contacting the hair after (2) with a shampoo and/or a conditioner, followed by rinsing with water.

The ionic liquids and the hair care compositions comprising the ionic liquids are unique in their ability to preserve hair fiber integrity, such that hair fibers treated with the ionic liquids or the hair care compositions comprising the ionic liquids have hair fiber integrity and other properties very similar to that of natural hair. This is because the ionic liquids are gentle to the hair and cause little if any damage to the hair fibers. Accordingly, the ionic liquids and the hair care compositions comprising the ionic liquids are useful in methods for preserving hair fiber integrity, such that the hair fiber integrity remains similar or substantially identical to natural hair. The methods include treating the hair with the ionic liquids or the hair care compositions comprising the ionic liquids and retaining hair fiber integrity.

As mentioned previously, the ionic liquids and the hair care compositions comprising the ionic liquids have little or no objectionable odor. Thiolactic acid and its salts are known to have a distinct unpleasant odor. However, when thiolactic acid and/or its salts are converted into an ionic liquid, which can be further incorporated into a hair care composition comprising the ionic liquid, the objectionable odor associated with the thiolactic acid and/or its salts is eliminated or greatly reduced. Thus, the ionic liquids and the hair care compositions comprising the ionic liquids are not only effective and gentle, but additionally do not exhibit an objectionable odor. Accordingly, the instant disclosure relates to methods for reducing odor of a hair care composition, the method comprising forming an ionic liquid, and adding the ionic liquid a hair care composition.

Moreover, the instant disclosure relates methods of treating hair using the ionic liquids or hair care compositions comprising the ionic liquids described herein. For example, the instant disclosure relates to imparting to the hair one or more of straightening effects; manageability; frizz control; volume reduction or volume control; styling effects; curling effects; relaxing effects; improvement or retention of curl definition; humidity resistance; and/or improvement of the appearance of hair.

The ionic liquids may be packaged independently from the remainder of the hair care composition (the remainder of the hair care composition referred to as "a cosmetically acceptable carrier"). The separately packaged ionic liquid may be added to the cosmetically acceptable carrier immediately before application to the hair. Many types of packaging for the ionic liquid are envisioned. For example, the ionic liquid may simply be packaged in a separate bottle or container, or separately packaged in a single multi-unit container, wherein the ionic liquid exists in one unit and the cosmetically acceptable carrier exists in a separate unit of the same container.

In some instances, the ionic liquid is packaged in an ampoule, typically a hermetically sealed ampoule. The pH of the ionic liquid is typically from about 3 to about 7, from about 3 to about 6, from about 3 to about 5, from about 4 to about 7, from about 4 to about 6, from about 4 to about 5, or from about 5 to about 6. Furthermore, the molar ratio of the thiolactate anion to the one or more ammonium cation compounds (cation) (in monomeric or polymeric form) is about 1:1.

The ionic liquid may include components that help stabilizer or preserve the ionic association between the thiolactate anion and the one or more ammonium cationic compounds (ammonium cation). For example, one or more antioxidants and/or one or more chelating agents may be included.

Examples of antioxidants include any cosmetically acceptable antioxidants, including but not limited to butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, sodium hydrogen sulfite, sodium sulfite, erythorbic acid, tocopherol acetate, dibutylhydroxytoluene, tocopherol, sodium metabisulfite, butylhydroxyanisole, propyl gallate, and mixtures thereof.

The total amount of the one or more antioxidants in the ionic liquid is about 0.001 wt. % to about 5 wt. %, based on the total weight of the ionic liquid. The total amount of the one or more antioxidants in the ionic liquid may be about 0.001 wt. % to about 4 wt. %, about 0.001 wt. % to about 3 wt. %, about 0.001 wt. % to about 2 wt. %, about 0.001 wt. % to about 1 wt. %. Likewise, the total amount of the one or more antioxidants in the ionic liquid may be about 0.01 wt. % to about 5 wt. %, about 0.01 wt. % to about 4 wt. %, about 0.01 wt. % to about 3 wt. %, about 0.01 wt. % to about 2 wt. %, about 0.01 wt. % to about 1 wt. %. Furthermore, the total amount of the one or more antioxidants may be about 0.1 wt. % to about 5 wt. %, about 0.1 wt. % to about 4 wt. %, about 0.1 wt. % to about 3 wt. %, about 0.1 wt. % to about 2 wt. %, about 0.1 wt. % to about 1 wt. %. Finally, the total amount of the one or more antioxidants may be from about 1 wt. % to about 5 wt. %, about 1 wt. % to about 4 wt. %, about 1 wt. % to about 3 wt. %, about 1 wt. % to about 2 wt. %.

Examples of chelating agents include α-hydroxy-fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide), and mixtures thereof.

The total amount of the one or more chelating agents in the ionic liquid is about 0.001 wt. % to about 5 wt. %, based on the total weight of the ionic liquid. The total amount of the one or more chelating agents in the ionic liquid may be about 0.001 wt. % to about 4 wt. %, about 0.001 wt. % to about 3 wt. %, about 0.001 wt. % to about 2 wt. %, about 0.001 wt. % to about 1 wt. %. Likewise, the total amount of the one or more chelating agents in the ionic liquid may be about 0.01 wt. % to about 5 wt. %, about 0.01 wt. % to about 4 wt. %, about 0.01 wt. % to about 3 wt. %, about 0.01 wt. % to about 2 wt. %, about 0.01 wt. % to about 1 wt. %. Furthermore, the total amount of the one or more chelating agents may be about 0.1 wt. % to about 5 wt. %, about 0.1 wt. % to about 4 wt. %, about 0.1 wt. % to about 3 wt. %, about 0.1 wt. % to about 2 wt. %, about 0.1 wt. % to about 1 wt. %. Finally, the total amount of the one or more chelating agents may be from about 1 wt. % to about 5 wt. %, about 1 wt. % to about 4 wt. %, about 1 wt. % to about 3 wt. %, about 1 wt. % to about 2 wt. %. The ampoule comprising the ionic liquid is often part of a kit. The kit is therefore useful in methods for making a ready-to-use hair care composition, wherein the method comprises mixing the content of the ampoule with a cosmetically acceptable carrier to form a ready-to-use hair care compositions, which can subsequently be applied to the hair for treatment. The ampoule can be used in methods for shaping hair, altering the shape of hair, and/or for caring for the hair, the methods comprising: (1) mixing the ionic liquid of the ampoule a cosmetically acceptable carrier to form a ready-to-use hair care composition; (2) applying the ready-to-use hair care composition onto hair; (3) optionally, brushing, combing, or smoothing the hair; (4) optionally, rinsing the hair; (5) heating the hair at to temperature of at least 25° C., 30° C., 35° C., 40° C., 45° C., or 50° C., while optionally applying a smoothing action to the hair; and (6) optionally, rinsing the hair with water. After mixing the content of the ampoule with the cosmetically acceptable carrier, the ready-to-use hair care compositions is typically applied to the hair within about 30 min., about 20 min., about 15 min., about 10 min., or about 5 min.

Ionic Mixtures

With respect to ionic mixtures, a typical hair care composition according to the instant disclosure comprises: (a) an ionic mixture comprising thiolactic acid and/or one or more alkali metal or alkaline earth metal salts thereof, and one or more amine compounds, one or more ammonium cationic compounds, and/or one or more salts thereof; (b) optionally, one or more neutralizing agents, wherein the neutralizing agent is different from the one or more ammonium cationic compounds and/or one or more salts thereof in (a); and (c) a cosmetically acceptable carrier. The pH of the hair care composition is typically from about 3 to about 10, about 3 to about 8, about 3 to about 7, from about 3 to about 6, from about 3 to about 5, from about 4 to about 7, from about 4 to about 6, from about 4 to about 5, or from about 5 to about 6.

The total amount of the thiolactic acid and/or one or more alkali metal or alkaline earth metal salts thereof and the total amount of the one or more amine compounds and/or one or more ammonium cationic compounds and/or one or more salts thereof can vary. For example, in some cases, the molar ratio of the total amount of the thiolactic acid and/or one or more alkali metal and/or alkaline earth metal salts thereof to the total amount of the one or more amine compounds and/or one or more ammonium cationic compounds and/or one or more salts thereof in the ionic mixture is about 10:1 to 1:10, about 8:1 to about 1:8, about 5:1 to about 1:5, about 3:1 to about 1:3, about 2:1 to about 1:2, or about 1:1. In some cases the molar amount of the thiolactic acid and/or one or more alkali metal and/or alkaline earth metal salts thereof is greater than the molar amount of the one or more amine compounds and/or the one or more ammonium cationic compounds and/or one or more salts thereof. For example, the molar ratio of the total amount of the thiolactic acid and/or one or more alkali metal and/or alkaline earth metal salts thereof to the total amount of the one or more amine compounds and/or one or more ammonium cationic compounds and/or one or more salts thereof in the ionic mixture may be from about 1:1 to about 10:1, about 1:1 to about 5:1, about 1:1 to about 4:1, about 1:1 to about 3:1, or about 1:1 to about 2:1.

In some cases, the thiolactic acid and/or one or more alkali metal and/or alkaline earth metal salts thereof used to form the ionic mixture is selected from the group consisting of thiolactic acid, sodium thiolactic acid (sodium thiolactate), potassium thiolactic acid (potassium thiolactate), magnesium thiolactic acid (magnesium thiolactate), strontium thiolactic acid (strontium thiolactate), calcium thiolactic acid (calcium thiolactate), and mixtures thereof.

Non-limiting examples of useful amines for forming an ionic mixutres include N,N,N-trimethylhydroxyethylammonium chloride (choline chloride), choline hydroxide, triethanolamine, monethanolamine, and mixtures thereof.

Likewise, in some cases, the one or more ammonium cationic compounds used to form the ionic mixture include one or more compounds and/or salts of formula (I):

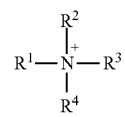

Formula (I)

in which $R^1$, $R^2$, $R^3$ and $R^4$ are independently hydrogen, phenyl, benzyl, a saturated, branched or unbranched alkyl residue with a chain length of 1 to 30 carbon atoms, which may optionally be substituted with one or more hydroxyl groups, thiol groups, carboxylic groups, and/or aryl groups, wherein the alkyl residue with a chain length of 1 to 30 carbon atoms may be interrupted by one or more oxygen atoms, sulfur atoms, and/or NR groups, wherein R is hydrogen or a saturated, branched or unbranched alkyl residue with a chain length 1 to 6; and wherein at least one of $R^1$, $R^2$, $R^3$ and $R^4$ is not hydrogen.

The one or more ammonium cationic compounds and/or salts thereof may include one or more compounds and/or salts of formula (I) (above), wherein $R^1$, $R^2$, $R^3$ and $R^4$ are independently hydrogen or a saturated, branched or unbranched alkyl residue with a chain length of 1 to 10 carbon atoms, which may optionally be substituted with one or more hydroxyl groups, thiol groups, carboxylic groups, and/or aryl groups, wherein the alkyl residue with a chain length of 1 to 10 carbon atoms may be interrupted by one or more oxygen atoms, sulfur atoms, and/or NR groups, wherein R is hydrogen or a saturated, branched or unbranched alkyl residue with a chain length 1 to 6; and wherein at least one of $R^1$, $R^2$, $R^3$ and $R^4$ is not hydrogen.

The one or more ammonium cationic compounds and/or salts thereof may include one or more compounds and/or salts of formula (I) (above), wherein $R^1$, $R^2$, $R^3$ and $R^4$ are independently hydrogen or a saturated, branched or unbranched alkyl residue with a chain length of 1 to 10 carbon atoms, which may optionally be substituted with one or more hydroxyl groups, thiol groups, or carboxylic groups, wherein the alkyl residue with a chain length of 1 to 10 carbon atoms may be interrupted by one or more oxygen atoms or sulfur atoms; and wherein at least one of $R^1$, $R^2$, $R^3$ and $R^4$ is not hydrogen.

Additionally, the one or more ammonium cationic ammonium compounds and/or salts thereof may be a cationic imidazolium compound of formula (II)

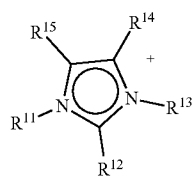

Formula II wherein $R^{11}$ and $R^{13}$ are the same or different and are each selected from the group consisting of an alkyl group of 1 to 10 or 1 to 6 carbon atoms, a cycloalkyl group of 4 to 10 carbon atoms, an aryl group of 6 to 10 carbon atoms, and a tri(C1-C10)alkylsilyl group, $R^{12}$ is selected from the group consisting of hydrogen, an alkyl group of 1 to 10 or 1 to 6 carbon atoms, a cycloalkyl group of 4 to 10 carbon atoms, an aryl group of 6 to 10 carbon atoms and a halogen atom; in some cases, $R^{12}$ is an alkyl group, a cycloalkyl group or an aryl group as defined above, $R^{14}$ and $R^{15}$ are the same or different and are each selected from the group consisting of hydrogen, an alkyl group of 1 to 10 or 1 to 6 carbon atoms, a cycloalkyl group of 4 to 10 carbon atoms, an aryl group of 6 to 10 carbon atoms, a tri(C1-C10)alkylsilyl group, and a halogen atom; in some cases $R^{14}$ and $R^{15}$ are the same or different and are hydrogen, an alkyl group, a cycloalkyl group, an aryl group, or a tri(C1-C10)alkylsilyl group; in some cases $R^{14}$ and $R^{15}$ are hydrogen.

The aforementioned alkyl group having 1 to 10 carbon atoms (sometimes abbreviated as "C1-C10"), or 1 to 6 carbon atoms (sometimes abbreviated as "C1-C6") in the definitions of $R^1$ to $R^{15}$ include optionally substituted linear or branched alkyl groups, such as methyl, ethyl, n-propyl, isopropyl, n-butyl, iso-butyl, sec-butyl, tert-butyl, n-pentyl, iso-pentyl, neo-pentyl, n-hexyl, n-heptyl, n-octyl, n-nonyl and n-decyl. Alkyl groups may be substituted by one or more substituents, identical or different. Among these substituents are halogen atoms. In some cases, alkyl groups with 1 to 6-carbon atoms are used, e.g. methyl, ethyl, propyl, iso-propyl, butyl, sec-butyl, iso-butyl, tert-butyl, 1-pentyl, 2-pentyl, 3-pentyl, iso-amyl, n-hexyl and iso-hexyl. In some cases, preferred substituted alkyl groups are haloalkly and perhaloalkyl, e.g. trifluoromethyl, 1,1,1-trifluoroethyl, perfluoroethyl, perfluoropropyl, 1,1,1,2,2,3,3-heptafluorobutyl and perfluorobutyl.

The aforementioned cycloalkyl group of 6 to 10 carbon atoms includes for example cyclobutyl, cyclopentyl, cyclohexyl, cycloheptyl, and cyclo-octyl, as well as bicycloalkyl groups, e.g. bicyclo[3.3.0]octyl, bicyclo[4.3.0]nonyl, bicyclo[4.4.0]decyl and bicyclo[2.2.1]heptyl. Tricycloakyl groups, for example adamantyl, are included in the definition of cycloalkyl. Cycloalkyl groups may be substituted by one or more identical or different substituents chosen, for example, from among alkyl groups and halogen atoms.

The aforementioned aryl group of 6 to 10 carbon atoms includes for example phenyl or naphthyl. Aryl groups may bear one or more substituents, identical or different.

With respect to the above mentioned (C1-C6) alkyl moiety of the tri(C1-C6)alkylsilyl group it is referred to the definition of the (C1-C6)alkyl groups for $R^{11}$ to $R^{15}$.

Halogen atoms in the above definitions include for example fluorine, chlorine, bromine and iodide.

With respect to the aforementioned (C1-C10)alkyl moiety in the definitions "bis-perfluoro(C1-C10)alkylsulphonyl amide" and "perfluoro(C1-C10)alkyl sulphonate" it is referred to the definition of the C1-C10 alkyl groups for $R^1$ to $R^{15}$ above.

In some instances, preferred imidazolium compounds of formula (II) are those having the following characteristics taken alone or in combination: $R^{11}$, $R^{12}$ and $R^{13}$, identical or different, are each independently chosen from (C1-C6)alkyl, (C1-C6)haloalkyl and cycloalkyl; $R^{14}$ and $R^{15}$, identical or different, are each independently chosen from hydrogen, (C1-C6)alkyl, (C1-C6)haloalkyl and cycloalkyl.

In some cases, preferred imidazolium compounds of formula (II) have the following characteristics taken alone or in combination: $R^{11}$, $R^{12}$ and $R^{13}$, identical or different, are each independently chosen from methyl, ethyl, propyl, iso-propyl, butyl, sec-butyl, 1-pentyl, 2-pentyl, 3-pentyl, iso-pentyl, hexyl, iso-hexyl, cyclohexyl, trifluoromethyl, 1,1,1-trifluoroethyl, perfluoroethyl, perfluoropropyl, 1,1,1,2,2,3,3-heptafluorobutyl, and perfluorobutyl; $R^{14}$ and $R^{15}$, identical or different, are each independently chosen from hydrogen, methyl, ethyl, propyl, iso-propyl, butyl, sec-butyl, 1-pentyl, 2-pentyl, 3-pentyl, iso-pentyl, hexyl, iso-hexyl, cyclohexyl, trifluoromethyl, 1,1,1-trifluoroethyl, perfluoroethyl, perfluoropropyl, 1,1,1,2,2,3,3-heptafluorobutyl, and perfluorobutyl.

In some cases, the compound(s) of formula (II) are 1,2,3-tri(C1-C10)alkyl-imidazolium salts. With respect to the aforementioned (C1-C10) alkyl moiety in the "1,2,3-tri(C1-C10)-alkyl-imidazolium salts" it is referred to the definition of the C1-C10 alkyl groups for $R^{11}$ to $R^{15}$ above.

In some cases, the compounds of formula (II) include 1-ethyl-2,3-dimethylimidazolium bromide ([EMMI][Br]), 1-ethyl-2,3-dimethylimidazolium bistrifluoromethylsulphonylamide ([EMMI][Tf$_2$N]), 1-ethyl-2,3-dimethylimidazolium trifluoromethylsulphonate ([EMMI][CF$_3$SO$_3$]), 1-n-butyl-2,3-dimethylimidazolium chloride ([BMMI][Cl]), 1-n-butyl-2,3-dimethylimidazolium hexafluorophosphate ([BMMI][PF$_6$]), 1-n-butyl-2,3-dimethylimidazolium bistrifluoromethylsulphonylamide ([BMMI][Tf$_2$N]), and 1-n-butyl-2,3-methylimidazolium tetrafluoroborate ([BMMI][BF$_4$]).

In some cases, the following compounds may be used 1-n-butyl-2,3-dimethylimidazolium salt is used, and more specifically 1-n-butyl-2,3-dimethylimidazolium chloride, 1-n-butyl-2,3-dimethylimidazolium hexafluorophosphate, 1-n-butyl-2,3-dimethylimidazolium bistrifluoromethylsulphonylamide and/or 1-n-butyl-2,3-methylimidazolium tetrafluoroborate.

Furthermore, in some instances, the one or more ammonium cationic compounds and/or salts thereof may be a cationic imidazolium compound of formula (III)

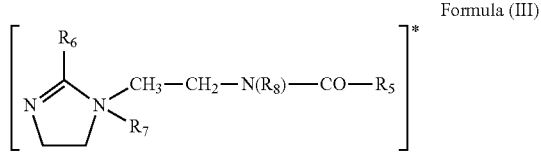

wherein $R_5$ and $R_6$ are chosen from alkenyl and alkyl radicals comprising from 1 to 30 carbon atoms or alkenyl and alkyl radicals derived from palm oil or hydrogenated tallow; $R_6$ is chosen from hydrogen, C1-C4 alkyl radicals, and alkenyl and alkyl radicals comprising from 8 to 30 carbon atoms; $R_7$ is chosen from C1-C4 alkyl radicals; and $R_8$ is chosen from hydrogen and C1-C4 alkyl radicals. If an anion is present, it may be chosen from, for example, halides, phosphates, acetates, lactates, alkyl sulfates, alkyl sulfonates, and alkylaryl sulfonates. Non-limiting examples of cationic imidazolium compounds of formula (III) include quaternium-83, quaternium-87, and mixtures thereof.

Furthermore, in some instances, the one or more ammonium cationic compounds and/or salts thereof may be polyammonium cationic compounds (two or more ammonium groups) such as diammonium and triammonium cationic compounds. Such compounds may be organic acid salts such as diammonium citrate or inorganic salts such as diammonium phosphate or diammonium sulfate.

Additionally, in some cases, the one or more amine compounds used to form the ionic mixture include alkyl amine compounds, alkylene amine compounds, and mixtures thereof. In some cases, the alkyl or alkylene group is from 2 to 4 carbon atoms. In yet other cases, the amine compounds are chosen from monoamine and polyamine compounds. The one or more amine compounds used to form the ionic mixtures can become cationic when neutralized, for example, with an acid that forms the anion part of the ionic liquid.

More specifically, the one or more amine compounds and/or the one or more ammonium cationic compounds and/or salts thereof may be selected from the group consisting of a betaine (trimethylglycine or 1-Carboxy-N,N,N-Trimethylmethanaminium Hydroxide, Inner Salt), carnitine (Ammonium, (3-carboxy-2-hydroxypropyl)trimethyl-, hydroxide, inner salt, L-), choline salt (N,N,N-trimethylhydroxyethylammonium or 2-Hydroxy-N,N,N-trimethyl-ethan-1-aminium salt) tris-(2-hydroxyethyl) methylammonium salt, tetramethylammonium salt, tetraethylammonium salt, diethyldimethylammonium salt, bis-(2-hydroxyethyl) dimethylammonium salt, tetrabutylammonium salt, tetrapropylammonium salt, triethanolamine (TEA), monoethanolamine (MEA), and mixtures thereof.

The salts of the one or more ammonium cationic compounds of the present invention are alkali metal or alkaline earth metal salts or salts of organic acids.

The one or more ammonium cationic compounds of the present invention may also be hydroxide compounds.

Various amounts of ionic mixtures can be added to cosmetically acceptable carriers to form hair care compositions. In some cases, the ionic mixture can be added to a cosmetically acceptable carrier such that about half of the hair care composition comprises the ionic mixture. Thus, in some cases, about 1 wt. % to about 50 wt. % of ionic mixture is combined with a cosmetically acceptable carrier to form a hair care compositions, wherein the weight percentages are based on the total weight of the hair care composition. Likewise, about 1 wt. % to about 45 wt. %, about 1 wt. % to about 40 wt. %, about 1 wt. % to about 35 wt. %, about 1 wt. % to about 30 wt. %, about 1 wt. % to about 25 wt. %, about 1 wt. % to about 20 wt. %, about 1 wt. % to about 15 wt. %, or about 1 wt. % to about 10 wt. % of ionic mixture is combined with a cosmetically acceptable carrier to form a hair care compositions, wherein the weight percentages are based on the total weight of the hair care composition. Furthermore, about 2 wt. % to about 45 wt. %, about 2 wt. % to about 40 wt. %, about 2 wt. % to about 35 wt. %, about 2 wt. % to about 30 wt. %, about 2 wt. % to about 25 wt. %, about 2 wt. % to about 20 wt. %, about 2 wt. % to about 15 wt. %, or about 2 wt. % to about 10 wt. % of ionic mixture is combined with a cosmetically acceptable carrier to form a hair care compositions, wherein the weight percentages are based on the total weight of the hair care composition. Additionally, about 3 wt. % to about 45 wt. %, about 3 wt. % to about 40 wt. %, about 3 wt. % to about 35 wt. %, about 3 wt. % to about 30 wt. %, about 3 wt. % to about 25 wt. %, about 3 wt. % to about 20 wt. %, about 3 wt. % to about 15 wt. %, or about 3 wt. % to about 10 wt. % of ionic mixture is combined with a cosmetically acceptable carrier to form a hair care compositions, wherein the weight percentages are based on the total weight of the hair care composition.

The hair care composition may optionally include one or more neutralizing agents. Non-limiting examples of neutralizing agents include organic amines, alkali metal hydroxides, alkali earth metal hydroxides, alkali metal carbonates, alkali metal phosphates, and mixtures thereof, and preferably selected from aminomethyl propanol, sodium hydroxide, potassium hydroxide, lithium hydroxide, aminomethyl propanediol, triisopropanol amine, dimethylstearylamine, dimethyl/tallowamine, lysine, ornithine, arginine, monoethanolamine, triethanolamine, calcium hydroxide, calcium bicarbonate, and mixtures thereof. In some cases, the one or more neutralizing comprises aminomethyl propanol, sodium hydroxide, monoethanolamine, or a mixture thereof. Typically, the total amount of the one or more neutralizing agents is about 0.1 wt. % to about 10 wt. %, based on the total weight of the hair care composition. Likewise, the total amount of the one or more neutralizing agent may be about 0.1 wt. % to about 8 wt. %, about 0.1 wt. % to about 7 wt. %, about 0.1 wt. % to about 6 wt. %, about 0.1 wt. % to about 5 wt. %, about 0.1 wt. % to about 4 wt. %, about 0.1 wt. % to about 3 wt. %, about 0.1 wt. % to about 2 wt. %. The total amount of the one or more neutralizing agents may also be from about 0.5 wt. % to about 10 wt. %, about 0.5 wt. % to about 8 wt. %, about 0.5 wt. % to about 7 wt. %, about 0.5 wt. % to about 6 wt. %, about 0.5 wt. % to about 5 wt. %, about 0.5 wt. % to about 4 wt. %, about 0.5 wt. % to about 3 wt. %, about 0.5 wt. % to about 2 wt. %.

The hair care compositions of the instant disclosure typically include about 1 wt. % to about 25 wt. % of the thiolactic acid and/or one or more alkali metal or alkaline earth metal salts thereof and a total amount of about 1 wt. % to about 25 wt. % of the one or more ammonium cationic compounds. The total amount of the thiolactic acid and/or one or more alkali metal or alkaline earth metal salts thereof in the hair care compositions may be about 1 wt. % to about 20 wt. %, about 1 wt. % to about 15 wt. %, about 1 wt. % to about 12 wt. %, about 1 wt. % to about 10 wt. %, or about 1 wt. % to about 8 wt. %. Likewise, the total amount of the thiolactic acid and/or one or more alkali metal or alkaline earth metal salts thereof in the hair care compositions may be about 2 wt. % to about 25 wt. %, about 2 wt. % to about 20 wt. %, about 2 wt. % to about 15 wt. %, about 2 wt. % to about 12 wt. %, about 2 wt. % to about 10 wt. %, or about 2 wt. % to about 8 wt. %. Furthermore, the total amount of the thiolactic acid and/or one or more alkali metal or alkaline earth metal salts thereof in the hair care compositions may be about 3 wt. % to about 25 wt. %, about 3 wt. % to about 20 wt. %, about 3 wt. % to about 15 wt. %, about 3 wt. % to about 12 wt. %, about 3 wt. % to about 10 wt. %, or about 3 wt. % to about 8 wt. %.

The total amount of the one or more ammonium cationic compounds in the hair care compositions may be about 1 wt. % to about 20 wt. %, about 1 wt. % to about 15 wt. %, about 1 wt. % to about 12 wt. %, about 1 wt. % to about 10 wt. %, or about 1 wt. % to about 8 wt. %. Likewise, the total amount of the one or more ammonium cationic compounds in the hair care compositions may be about 2 wt. % to about 25 wt. %, about 2 wt. % to about 20 wt. %, about 2 wt. % to about 15 wt. %, about 2 wt. % to about 12 wt. %, about 2 wt. % to about 10 wt. %, or about 2 wt. % to about 8 wt. %. Furthermore, the total amount of the one or more ammonium cationic in the hair care compositions may be about 3 wt. % to about 25 wt. %, about 3 wt. % to about 20 wt. %, about 3 wt. % to about 15 wt. %, about 3 wt. % to about 12 wt. %, about 3 wt. % to about 10 wt. %, or about 3 wt. % to about 8 wt. %.

The hair care compositions of the instant disclosure include an ionic mixture, which is typically combined with a cosmetically acceptable carrier. The combination of the ionic mixture and the cosmetically acceptable carrier typically results in a ready-to-use hair care compositions. The hair care compositions may be pre-mixed and sold as a single ready-to-use product, or may be supplied in the form of a kit, wherein the ionic mixture is separated from the cosmetically acceptable carrier, and the ionic mixture and the cosmetically acceptable carrier are mixed immediately before application to the hair to form a ready-to-use hair care composition. For example, the ionic mixture may be added and mixed to the cosmetically acceptable carrier and applied to the hair within about 30 min., about 20 min., about 15 min., about 10 min., or about 5 min.

In some instances, the cosmetically acceptable carrier is anhydrous or essentially anhydrous. The term "essentially anhydrous" indicates that the composition contains about 5 wt. % of less of water. In some cases, the anhydrous cosmetically acceptable carrier comprises about 4 wt. %, about 3 wt. %, about 2 wt. %, or about 1 wt. % or less of water. The total amount of the anhydrous cosmetically acceptable carrier may be 50 to 96 wt. %, based on the total weight of the hair care composition. Further, the total amount of the anhydrous cosmetically acceptable carrier may be about 50 to about 95 wt. %, about 50 to about 92 wt. %, about 50 to about 90 wt. %, about 50 to about 85 wt. %, about 50 to about 80 wt. %, 55 to about 95 wt. %, about 55 to about 92 wt. %, about 55 to about 90 wt. %, about 55 to about 85 wt. %, about 55 to about 80 wt. %, about 60 to about 95 wt. %, about 60 to about 92 wt. %, about 60 to about 90 wt. %, about 60 to about 85 wt. %, or about 60 to about 80 wt. %.

Anhydrous component useful as part of the anhydrous cosmetically acceptable carrier include, for example, mixture polyols such as polyethylene glycol, propylene glycol, butylene glycol, hexylene glycol, glycerin, diglycerin, diethylene glycol, dipropylene glycol, and mixtures thereof; mixture paraffin; mineral oil; vegetable oil; ester oils such as pentaerythritol ester oils, trimethylol ester oils, citrate ester oils, glyceryl ester oils, and mixtures thereof. The polyethylene glycols useful herein are those having the formula:

$$H(OCH_2CH_2)_n\text{---}OH$$

wherein n has an average value of from 4 to 12. The polyethylene glycol described above is also known as a polyethylene oxide, and polyoxyethylene. Polyethylene glycols useful herein include PEG-200 wherein n has an average value of about 4.

The cosmetically acceptable carrier may also be aqueous. In addition to water, the aqueous carrier may include water soluble components, such as glycerin, $C_{1-4}$ alcohols, organic solvents, polyols, glycols, and combinations thereof. The total amount of the aqueous cosmetically acceptable carrier may be 50 to 96 wt. %, based on the total weight of the hair care composition. Further, the total amount of the cosmetically acceptable carrier may be about 50 to about 95 wt. %, about 50 to about 92 wt. %, about 50 to about 90 wt. %, about 50 to about 85 wt. %, about 50 to about 80 wt. %, 55 to about 95 wt. %, about 55 to about 92 wt. %, about 55 to about 90 wt. %, about 55 to about 85 wt. %, about 55 to about 80 wt. %, about 60 to about 95 wt. %, about 60 to about 92 wt. %, about 60 to about 90 wt. %, about 60 to about 85 wt. %, or about 60 to about 80 wt. %.

In some instances, the hair care composition of the instant disclosure is in the form of an emulsion, for example, oil in water emulsion (O/W emulsion) or water in oil (W/O emulsion). When the hair care composition is in the form of an emulsion, both an aqueous cosmetically acceptable carrier and an anhydrous cosmetically acceptable carrier exist. In other words, the hair care composition includes an aqueous phase and a fatty phase. Typically, the ionic mixtures will be added to anhydrous phase (or the fatty phase) of the emulsion.

The hair care compositions of the instant disclosure may be in the form of a gel or a cream and independently may have a viscosity of about 405 to about 450 cps or mPa·s), which corresponded to a texture and consistency of some gels. The gel texture provides the benefits of ease of application of the composition into the hair, spreadability of the composition on the hair, and/or ease of brushing or combing the hair. A hair care composition in the form of a gel or a cream does not readily drip off from the hair; the gel or cream remains adhered to the hair during processing with the hair care composition.

The instant disclosure relates to methods for making ionic mixtures and hair care compositions comprising ionic mixtures. For example, methods for making hair care compositions according to the instant disclosure include forming an ionic mixture and combining the ionic mixture with a cosmetically acceptable carrier, wherein forming the ionic mixture comprises: mixing thiolactic acid and/or one or more alkali metal or alkaline earth metal salts thereof with one or more amine compounds, one or more ammonium cationic compounds, and/or one or more salts thereof.

In addition to methods for making the hair care compositions, as described above, the instant disclosure also relates to hair care compositions made by the methods. For examples, hair care compositions manufactured by forming an ionic mixture and combining the ionic mixture with a cosmetically acceptable carrier, wherein forming the ionic mixture is described above.

The ionic mixtures and the hair care compositions comprising the ionic mixtures are useful for shaping hair, altering the shape of hair, and for caring for the hair. Accordingly, the instant disclosure is directed to methods for shaping hair, altering the shape of hair, and for caring for the hair, the methods comprising: (1) applying a hair care composition as described herein to hair; (2) optionally, brushing, combing, or smoothing the hair; (3) optionally, rinsing the hair; (4) heating the hair at to temperature of at least 25° C., 30° C., 35° C., 40° C., 45° C., or 50° C., while optionally applying a smoothing or shaping action to the hair; and (5) optionally, rinsing the hair with water. The methods an further comprise contacting the hair after (2) with a shampoo and/or a conditioner, followed by rinsing with water.

The ionic mixtures and the hair care compositions comprising the ionic mixtures are unique in their ability to preserve hair fiber integrity, such that hair fibers treated with the ionic mixtures or the hair care compositions comprising the ionic mixtures have hair fiber integrity and other properties very similar to that of natural hair. This is because the ionic mixtures are gentle to the hair and cause little if any damage to the hair fibers. Accordingly, the ionic mixtures and the hair care compositions comprising the ionic mixtures are useful in methods for preserving hair fiber integrity, such that the hair fiber integrity remains similar or substantially identical to natural hair. The methods include treating the hair with the ionic mixtures or the hair care compositions comprising the ionic mixtures and retaining hair fiber integrity.

Moreover, the instant disclosure relates methods of treating hair using the ionic mixtures or hair care compositions comprising the ionic mixtures. For example, the instant disclosure relates to methods for imparting to the hair one or more of straightening effects; manageability; frizz control; volume reduction or volume control; styling effects; curling effects; relaxing effects; improvement or retention of curl definition; humidity resistance; and/or improvement of the appearance of hair.

The ionic mixtures may be packaged separately from the remainder of the hair care composition (the remainder of the hair care composition referred to as "a cosmetically acceptable carrier"). The separately packaged ionic mixture may be added to the cosmetically acceptable carrier immediately before application to the hair. Many types of packaging for the ionic mixture are envisioned. For example, the ionic mixture may simply be packaged in a separate bottle or container, or separately packaged in a single multi-unit container, wherein the ionic mixture exists in one unit and the cosmetically acceptable carrier exists in a separate unit of the same container.

In some instances, the ionic mixture is packaged in an ampoule, typically a hermetically sealed ampoule. The pH of the ionic mixture is typically from about 3 to about 7, from about 3 to about 6, from about 3 to about 5, from about 4 to about 7, from about 4 to about 6, from about 4 to about 5, or from about 5 to about 6. Furthermore, the molar ratio of the total amount of the thiolactic acid and/or one or more alkali metal or alkaline earth metal salts thereof to the total amount of the one or more amine compounds, the one or more ammonium cationic compounds, and/or salts thereof, in the ionic mixture is about 10:1 to about 1:10. In some cases, the molar ratio is about 8:1 to about 1:8, about 5:1 to about 1:5, about 3:1 to about 1:3, about 2:1 to about 1:2, or about 1:1.

The ionic mixture may include components that help stabilizer and/or preserve the ionic mixture and/or the hair care compositions comprising the ionic mixture. For example, one or more antioxidants and/or one or more chelating agents may be included.

Examples of antioxidants include any cosmetically acceptable antioxidants, including but not limited to butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, sodium hydrogen sulfite, sodium sulfite, erythorbic acid, tocopherol acetate, dibutylhydroxytoluene, tocopherol, sodium metabisulfite, butylhydroxyanisole, propyl gallate, and mixtures thereof.

The total amount of the one or more antioxidants in the ionic mixture is about 0.001 wt. % to about 5 wt. %, based on the total weight of the ionic mixture. The total amount of the one or more antioxidants in the ionic mixture may be about 0.001 wt. % to about 4 wt. %, about 0.001 wt. % to about 3 wt. %, about 0.001 wt. % to about 2 wt. %, about 0.001 wt. % to about 1 wt. %. Likewise, the total amount of the one or more antioxidants in the ionic mixture may be about 0.01 wt. % to about 5 wt. %, about 0.01 wt. % to about 4 wt. %, about 0.01 wt. % to about 3 wt. %, about 0.01 wt. % to about 2 wt. %, about 0.01 wt. % to about 1 wt. %. Furthermore, the total amount of the one or more antioxidants may be about 0.1 wt. % to about 5 wt. %, about 0.1 wt. % to about 4 wt. %, about 0.1 wt. % to about 3 wt. %, about 0.1 wt. % to about 2 wt. %, about 0.1 wt. % to about 1 wt. %. Finally, the total amount of the one or more antioxidants may be from about 1 wt. % to about 5 wt. %, about 1 wt. % to about 4 wt. %, about 1 wt. % to about 3 wt. %, about 1 wt. % to about 2 wt. %.

Examples of chelating agents include α-hydroxy-fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, ZnSO.sub.4), selenium and derivatives thereof (for example selenomethionine), stilbenes and derivatives thereof (for example stilbene oxide, trans-stilbene oxide), and mixtures thereof.

The total amount of the one or more chelating agents in the ionic mixture is about 0.001 wt. % to about 5 wt. %, based on the total weight of the ionic mixture. The total amount of the one or more chelating agents in the ionic mixture may be about 0.001 wt. % to about 4 wt. %, about 0.001 wt. % to about 3 wt. %, about 0.001 wt. % to about 2 wt. %, about 0.001 wt. % to about 1 wt. %. Likewise, the total amount of the one or more chelating agents in the ionic mixture may be about 0.01 wt. % to about 5 wt. %, about 0.01 wt. % to about 4 wt. %, about 0.01 wt. % to about 3 wt. %, about 0.01 wt. % to about 2 wt. %, about 0.01 wt. % to about 1 wt. %. Furthermore, the total amount of the one or more chelating agents may be about about 0.1 wt. % to about 5 wt. %, about 0.1 wt. % to about 4 wt. %, about 0.1 wt. % to about 3 wt. %, about 0.1 wt. % to about 2 wt. %, about 0.1 wt. % to about 1 wt. %. Finally, the total amount of the one or more chelating agents may be from about 1 wt. % to about 5 wt. %, about 1 wt. % to about 4 wt. %, about 1 wt. % to about 3 wt. %, about 1 wt. % to about 2 wt. %.

The ampoule comprising the ionic mixture is often part of a kit. The kit is therefore useful in methods for making a ready-to-use hair care composition, wherein the method comprises mixing the content of the ampoule with a cosmetically acceptable carrier to form a ready-to-use hair care compositions, which can subsequently be applied to the hair for treatment. The ampoule can be used in methods for shaping hair, altering the shape of hair, and/or for caring for the hair, the methods comprising: (1) mixing the ionic mixture of the ampoule a cosmetically acceptable carrier to form a ready-to-use hair care composition; (2) applying the ready-to-use hair care composition onto hair; (3) optionally, brushing, combing, or smoothing the hair; (4) optionally, rinsing the hair; (5) heating the hair at to temperature of at least 25° C., 30° C., 35° C., 40° C., 45° C., or 50° C., while optionally applying a smoothing or shaping action to the hair; and (6) optionally, rinsing the hair with water. After mixing the content of the ampoule with the cosmetically acceptable carrier, the ready-to-use hair care compositions is typically applied to the hair within about 30 min., about 20 min., about 15 min., about 10 min., or about 5 min.

More exhaustive but non-limiting lists of components useful in the ionic liquids and/or the hair care compositions described herein are presented below.

Neutralizing Agents

Suitable neutralizing agents may be selected from alkali metal carbonates, alkali metal phosphates, organic amines, hydroxide base compounds, and mixtures thereof, particularly from organic amines, alkali metal hydroxides, alkali earth metal hydroxides, and mixtures thereof.

Organic amines may be selected from amino-2-methyl-1-propanol (or aminomethyl propanol), ethylamines, ethyleneamines, alkanolamines, cyclic amines and other cyclic compounds, saturated or unsaturated, having one or more nitrogen atoms within the ring, and mixtures thereof.

The organic amines may be chosen from the ones having a pKb at 25° C. of less than 12, such as less than 10 or such as less than 6. It should be noted that this is the pKb corresponding to the function of highest basicity.

Organic amines may be chosen from organic amines comprising one or two primary, secondary, or tertiary amine functions, and at least one linear or branched C1-C8 alkyl groups bearing at least one hydroxyl radical.

Organic amines may also be chosen from alkanolamines such as mono-, di- or trialkanolamines, comprising one to three identical or different C1-C4 hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

Among the compounds of the alkanolamine type that may be mentioned include but not limited to: monoethanolamine (also known as monoethanolamine or MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane.

Other examples include but are not limited to: 1,3-diaminopropane, 1,3-diamino-2-propanol, spermine, and spermidine.

In some cases, the organic amines are chosen from amino acids.

As non-limiting examples, the amino acids that may be used may be of natural or synthetic origin, in L, D, or racemic form, and comprise at least one acid function chosen from, for instance, carboxylic acid, sulfonic acid, phosphonic acid, and phosphoric acid functions. The amino acids may be in their neutral or ionic form. Amino acids that may be used in the present disclosure include but are not limited to: aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

Further as non-limiting examples, the amino acids may be chosen from basic amino acids comprising an additional amine function optionally included in a ring or in a ureido function. Such basic amino acids may be chosen from histidine, lysine, arginine, ornithine, and citrulline.

In some cases, the organic amines are chosen from organic amines of heterocyclic type. Besides histidine that has already been mentioned in the amino acids, non-limiting mention may also be made of pyridine, piperidine, imidazole, 1,2,4-triazole, tetrazole, and benzimidazole.

In some instances, the organic amines are chosen from amino acid dipeptides. Amino acid dipeptides that may be used in the present disclosure include but not limited to: carnosine, anserine, and baleine.

In some cases, the organic amines are chosen from compounds comprising a guanidine function. Organic amines of this type that may be used in the present disclosure include, besides arginine that has already been mentioned as an amino acid, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

The alkali metal phosphates and carbonates that may be used are, for example, sodium phosphate, potassium phosphate, sodium carbonate, sodium bicarbonate, potassium carbonate, potassium bicarbonate, and their derivatives.

The hydroxide base compounds chosen from alkali metal hydroxides, alkaline-earth metal hydroxides, transition metal hydroxides, quaternary ammonium hydroxides, organic hydroxides, and mixtures thereof. Suitable examples are ammonium hydroxide, sodium hydroxide, potassium hydroxide, lithium hydroxide, rubidium hydroxide, caesium hydroxide, francium hydroxide, beryllium hydroxide, magnesium hydroxide, calcium hydroxide, strontium hydroxide, barium hydroxide, molybdenum hydroxide, manganese hydroxide, zinc hydroxide, cobalt hydroxide, cadmium hydroxide, cerium hydroxide, lanthanum hydroxide, actinium hydroxide, thorium hydroxide, aluminium hydroxide, guanidinium hydroxide and mixtures thereof.

The at least one neutralizing agent may be chosen from at least one organic amine such as at least one alkanolamine. Particularly preferred alkanolamines are 2-amino-2-methyl-1-propanol (aminomethyl propanol), ethanolamine (also known as monoethanolamine or MEA), triethanolamine, and mixtures thereof. An even more particularly preferred alkanolamine is ethanolamine.

According to at least one embodiment, the at least one neutralizing agent is chosen from aminomethyl propanol, sodium hydroxide, potassium hydroxide, lithium hydroxide, aminomethyl propanediol, triisopropanol amine, dimethylstearylamine, dimethyl/tallowamine, lysine, ornithine, arginine, monoethanolamine, triethanolamine, calcium hydroxide, calcium bicarbonate, and mixtures thereof.

According to another embodiment, the at least one neutralizing agent is chosen from aminomethyl propanol, sodium hydroxide, lithium hydroxide, calcium hydroxide, and mixtures thereof.

In some cases, the at least one neutralizing agent is selected from aminomethyl propanol and is present in an amount of from about 0.1% to about 6.3% by weight, from about 0.2% to about 5.5% by weight, from about 0.3% to about 5% by weight, or from about 0.3% to about 4.6% by weight, based on the total weight of the hair care composition, including all ranges and subranges there-between.

In certain instances, the at least one neutralizing agent is aminomethyl propanol. In some cases, the at least one neutralizing agent is sodium hydroxide and is present in an amount of from about 0.1% to about 4.1% by weight, from about 0.15% to about 3.5% by weight, from about 0.2% to about 3% by weight, or from about 1% to about 3% by weight, based on the total weight of the hair care composition, including all ranges and subranges there-between.

In certain instances, the at least one neutralizing agent is sodium hydroxide in an amount of about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, about 2.3%, 2.4%, 2.5%, 2.6%, 2.7%, 2.8%, 2.9%, 3%, based on the total weight of the hair care composition.

Antioxidants

Examples of antioxidants useful in the present disclosure include vitamin E (tocopherol), lecithin, wheat germ oil, sodium sulfite, sodium bisulfite, uric acid, propyl gallate, butylated hydroxyanisole (BHA), toluhydroquinone (THQ) sold as Tenox PG, Tenox BHA and Tenox THQ by Eastman Chemical Products Inc., and butylated hydroxytoluene (BHT) sold as Sustane BHT by UOP Process Division.

In some cases, one or more antioxidants are selected from the group consisting of: ascorbic acid (vitamin C), ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, peroxides including hydrogen peroxide, perborate, thioglycolates, persulfate salts, 6-hydroxy-2,5,7,8-tetramethylchroman-2-carboxylic acid (commercially available under the tradename Trolox™), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, 1-methionine, proline, superoxide dismutase, silymarin, tea extracts, grape skin and/or grape seed extracts, melanin, rosemary extracts, and mixtures thereof.

Chelating Agents

Examples of chelating agents useful in the present disclosure include the sodium, potassium and ammonium salts of diphosphoric acid, triphosphoric acid, pyrophosphoric acid, orthophosphoric acid, hexametaphosphoric acid, 1-hydroxyethane-1,1-phosphonic acid, diethylenetriamine penta (methylene diphosphonic acid), ethylenediamine tetraacetic acid (EDTA), diethylenetriamine pentaacetic acid (DTPA), N-(hydroxyethyl) ethylenediamine triacetic acid (HEDTA), propylenediamine tetraacetic acid (PDTA), nitrilotriacetic acid (NTA), mellitic acid, 1,2,3,4-cyclopentane tetracarboxylic acid, succinic acid, lauryl succinic acid, oxydisuccinic acid (ODS), carboxymethyloxysuccinic acid, citric acid, lactic acid, tartaric acid, O-carboxymethyltartronic acid, polyacrylic acid, poly(.alpha.-hydroxyacrylic acid), poly(tetramethylene-1,2-dicarboxylic acid), poly(4-methoxytetramethylene-1,2-dicarboxylic acid), acrylic acid/maleic acid copolymer (polycarboxylate), acrylic acid/allyl alcohol copolymer (polycarboxylate), sodium PCA, gluconic acid, glucoheptonic acid, lactobionic acid, maltobionic acid and mixtures thereof. Preferred are the sodium, potassium and ammonium salts of ethylenediamine tetraacetic acid, diethylenetriamine pentaacetic acid, and mixtures thereof.

Oils

The one or more oils typically include those generally used in cosmetics and particularly from oils of animal, vegetable or mineral origin, linear or branched hydrocarbons, optionally branched and/or unsaturated fatty acids, optionally branched and/or unsaturated fatty alcohols, mono- and/or polyesters of fatty acids and/or of fatty alcohols, perfluorinated and/or organofluorinated oils, volatile or non-volatile silicone oils, fluorosilicone oils and their mixtures.

Non-limiting examples of oils include oils of animal, vegetable or mineral origin, of lanolin, squalene, fish oil, perhydrosqualene, mink oil, turtle oil, soybean oil, grape seed oil, sesame oil, maize oil, rapeseed oil, sunflower oil, cottonseed oil, avocado oil, olive oil, castor seed oil, jojoba seed oil, peanut oil, sweet almond oil, palm oil, cucumber oil, hazelnut oil, apricot kernel oil, wheat germ oil, calophyllum oil, macadamia oil, coconut oil, cereal germ oil, candlenut oil, thistle oil, candelilla oil, safflower oil, shea butter, and their mixtures.

Mention is made, as an example of linear or branched hydrocarbons, of oils of mineral or synthetic origin, such as liquid paraffins and their derivatives, petrolatum, mineral oils, (mixtures of oil-derived hydrocarbon oils), polybutene, hydrogenated polyisobutene, polyisoprene, polydecenes such as hydrogenated polydecene, or also linear, branched and/or cyclic alkanes which are optionally volatile, such as, for example, isohexadecane, isododecane, isodecane or isohexadecane, and their mixtures.

Mention is made, as examples of optionally branched and/or unsaturated fatty acids, of myristic acid, palmitic acid, stearic acid, behenic acid, oleic acid, linoleic acid, linolenic acid or isostearic acid, and their mixtures.

Mention is made, as example of optionally branched and/or unsaturated fatty alcohols, of cetanol, stearyl alcohol, oleyl alcohol, cetyl alcohol, octyldodecanol, and their mixtures.

Mention is made, as examples of esters, of monoesters or polyesters of fatty acids, the linear or branched fatty chain of which includes from 6 to 30 carbon atoms, and of fatty alcohols, the fatty chain of which includes from 3 to 30 carbon atoms, in particular mono- and polyesters of hydroxy acids and of fatty alcohols, esters of benzoic acid and of fatty alcohols, polyesters of polyols, dipentaerythrityl $C_5$-$C_9$ esters, trimethylolpropane polyesters, propylene glycol polyesters, polyesters of hydrogenated castor oil.

Further mention is made of the oils of the group consisting of isononyl isononanoate, stearyl octanoate, isopropyl palmitate, isopropyl myristate, butyl stearate, hexyl laurate, 2-ethylhexyl palmitate, 2-hexyldecyl laurate, 2-octyldecyl palmitate, 2-octyldodecyl myristate, di(2-ethylhexyl) succinate, diisostearyl malate, 2-octyldodecyl lactate, glyceryl triisostearate or diglyceryl triisostearate, octyldodecyl stearoyl stearate (Ceraphyl), cetearyl isononanoate, diisopropyl adipate, caprylic/capric triglyceride, glyceryl tricaprate/caprylate, isocetyl stearoyl stearate, $C_{12}$-$C_{15}$ alkyl benzoates, pentaerythrityl tetraisostearate, dipentaerythrityl pentaisononanoate, bis-diglyceryl polyacyladipate-2, trimethylolpropane triethylhexanoate, propylene glycol dibenzoate, propylene glycol dioctanoate, and mixture thereof.

Mention is made, as example of volatile silicone oils, of hexamethyldisiloxane, dimethicones with a viscosity of between 0.65 and 5 mm²/s, octamethylcyclotetrasiloxane, heptamethylhexyltrisiloxane, decamethylcyclopentasiloxane, decamethyltetrasiloxane, octamethyltrisiloxane, dodecamethylcyclohexasiloxane, heptamethyloctyltrisiloxane, and their mixtures.

Mention is made, as example of non-volatile silicone oils, of non-volatile polydialkylsiloxanes; polydimethylsiloxanes comprising pendant alkyl, alkoxy or phenyl groups or alkyl, alkoxy or phenyl groups at the end of the silicone chain, which groups have from 2 to 24 carbon atoms; phenylated silicones, such as those of the phenyl trimethicone type, those of the phenylpropyldimethylsiloxysilicate type or those of the trimethylpentaphenyltrisiloxane type; polysiloxanes modified by fatty acids, in particular $C_8$-$C_{20}$ fatty acids, fatty alcohols, in particular $C_8$-$C_{20}$ fatty alcohols, or polyoxyalkylenes (in particular polyoxyethylene and/or polyoxypropylene); aminated polysiloxanes; polysiloxanes comprising a hydroxyl group; and their mixtures.

Mention is made, as fluorosilicone oils, of fluorinated polysiloxanes comprising a pendant fluorinated group or a fluorinated group at the end of the silicone chain having from 1 to 12 carbon atoms, all or a portion of the hydrogens of which are replaced by fluorine atoms, such as perfluorononyl dimethicone, and their mixtures.

Dimethicone Copolyol

The hair care compositions of the instant disclosure may include one or more dimethicone copolyols. The term "dimethicone copolyol," as used herein, includes a polymer made from dimethicone and polyoxyethylene and/or polyoxypropylene.

Dimethicone copolyols can also be described as silicone surfactants or as emulsifiers.

Suitable examples of dimethicone copolyols include Dimethicone PEG-8 Adipate, Dimethicone PEG-8 Benzoate, Dimethicone PEG-7 Phosphate, Dimethicone PEG-8 Phosphate, Dimethicone PEG-10 Phosphate, Dimethicone PEG/PPG-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11 Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and mixtures thereof.

While not wishing to be bound to any one theory, in some cases, the use of one or more dimethicone copolyols in the hair care compositions of the instant disclosure can help stabilize the composition.

Thus, a dimethicone copolyol that may be employed according to the disclosure is an oxypropylenated and/or oxyethylenated polydimethyl(methyl)siloxane. Use may be made, as dimethicone copolyol, of those corresponding to the following formula (I):

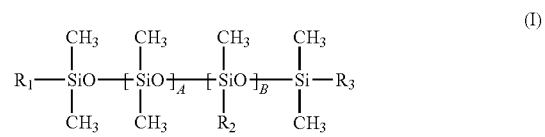

in which:

$R_1$, $R_2$ and $R_3$ represent, independently of one another, a $C_1$-$C_6$ alkyl radical or a —$(CH_2)x$-$(OCH_2CH_2)y$-$(OCH_2CH_2CH_2)z$-$OR_4$ radical, at least one $R_1$, $R_2$ or $R_3$ radical not being an alkyl radical; $R_4$ being a hydrogen, a $C_1$-$C_3$ alkyl radical or a $C_2$-$C_4$ acyl radical;

A is an integer ranging from 0 to 200;

B is an integer ranging from 0 to 50; provided that A and B are not equal to zero at the same time; x is an integer ranging from 1 to 6; y is an integer ranging from 1 to 30; z is an integer ranging from 0 to 5.

According to a preferred embodiment of the invention, in the compound of formula (I), $R=R_3$=methyl radical, x is an integer ranging from 2 to 6 and y is an integer ranging from 4 to 30. $R_4$ is in particular a hydrogen.

Mention may be made, as examples of compounds of formula (I), of the compounds of formula (II):

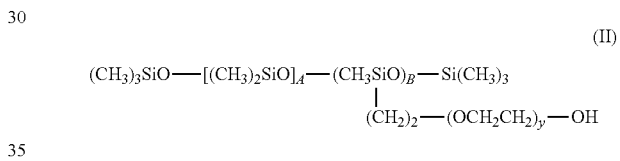

in which A is an integer ranging from 20 to 105, B is an integer ranging from 2 to 10 and y is an integer ranging from 10 to 20.

Mention may also be made, as examples of silicone compounds of formula (I), of the compounds of formula (III):

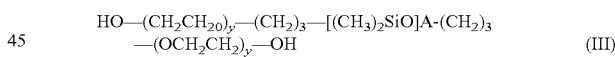

in which A' and y are integers ranging from 10 to 20.

Use may be made, as dimethicone copolyol, of those sold under the names DC 5329, DC 7439-146, DC 2-5695 and Q4-3667 by Dow Corning; and KF-6013, KF-6015, KF-6016, KF-6017 and KF-6028 by Shin-Etsu.

In some cases, the hair care compositions of the instant disclosure include, as a dimethicone copolyol, one of those sold under the names KF-6013, KF-6015, KF-6016, KF-6017 and KF-6028 by Shin-Etsu. In some cases, the dimethicone copolyol is PEG-12 dimethicone commercially available from Dow Corning under the trade name XIAMETER® OFX-0193 FLUID. The dimethicone copolyols can also be chosen from at least one $C_8$-$C_{22}$ alkyl dimethicone copolyol.

This $C_8$-$C_{22}$ alkyl dimethicone copolyol of the invention is more particularly an oxypropylenated and/or oxyethylenated polymethyl ($C_8$-$C_{22}$) alkyl dimethyl methyl siloxane.

The $C_8$-$C_{22}$ alkyl dimethicone copolyol may be a compound of the following formula (IV):

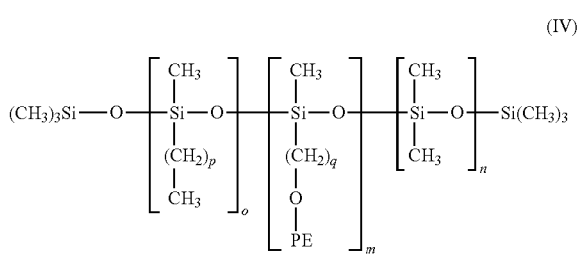

wherein:

PE represents from groups (—C$_2$H$_{40}$)x-(C$_3$H$_{60}$)$_y$—R, wherein R is chosen from a hydrogen atom and an alkyl radical comprising from 1 to 4 carbon atoms, x is an integer ranging from 0 to 100, and y is an integer ranging from 0 to 80, provided that x and y are not simultaneously equal to 0; and m is an integer ranging from 1 to 40, n is an integer ranging from 10 to 200, o is an integer ranging from 1 to 100, p is an integer ranging from 7 to 21, and q is an integer ranging from 0 to 4.

In some cases, R is a hydrogen atom, m is an integer ranging from 1 to 10, n is an integer ranging from 10 to 100, o is an integer ranging from 1 to 30, p is 15, and q is 3. In some cases, the at least one C$_8$-C$_{22}$ alkyl dimethicone copolyol is cetyl dimethicone copolyols such as the product marketed under the name Abil® EM-90 by the company Goldschmidt.

In some cases, the C$_8$-C$_{22}$ alkyl dimethicone copolyol is a cetyl dimethicone copolyol, for example, the product marketed under the name Abil® EM-90 by the company Goldschmidt (also known as cetyl PEG/PPG-10/1 dimethicone). In some cases, the hair care compositions comprise cetyl PEG/PPG-10/1 dimethicone as C8-C22 alkyl dimethicone copolyol and a mixture of dimethicone and dimethicone/vinyl dimethicone crosspolymer as organopolysiloxane elastomer not containing a hydrophilic chain. In some cases, the hair care compositions comprise a mixture of dimethicone and dimethicone/vinyl dimethicone crosspolymer as organopolysiloxane elastomer not containing a hydrophilic chain, a PEG-10 dimethicone as dimethicone copolyol, and a cetyl PEG/PPG-10/1 dimethicone as C8-C22 alkyl dimethicone copolyol.

Thus, in some cases, the dimethicone copolyol is chosen from oxypropylenated and/or oxyethylenated polydimethyl (methyl)siloxane, oxypropylenated and/or oxyethylenated polymethyl (C8-C22) alkyl dimethyl methyl siloxane, and mixtures thereof. In certain cases, the dimethicone copolyol is chosen from Dimethicone PEG-8 Benzoate, Dimethicone PEG-7 Phosphate, Dimethicone PEG-8 Phosphate, Dimethicone PEG-10 Phosphate, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-17/18 Dimethicone, cetyl PEG/PPG-10/1 dimethicone, and mixtures thereof. In other embodiments, the dimethicone copolyol is PEG-12 dimethicone, The dimethicone copolyols are generally present in the composition in an amount ranging from about 0.5% to about 5% by weight, from about 1% to about 4% by weight, from about 1.5% to about 3% by weight, or from about 2% to about 3% by weight, based on the total weight of the hair care composition, including all ranges and subranges therebetween. In certain instances, the total amount of the one or more dimethicone copolyols is in an amount of about 0.1%, or about 0.25%, or about 0.5%, or about 0.75%, or about 1% by weight, or about 1.1%, or about 1.2%, or about 1.3%, or about 1.4% by weight, or about 1.5% by weight, or about 1.6%, or about 1.7%, or about 1.8%, or about 1.9% by weight, or about 2% by weight, based on the total weight of the composition.

Emulsifiers

Emulsifiers are well known in the art and include amphoteric, anionic, cationic or nonionic emulsifiers, used alone or as a mixture, and optionally with a co-emulsifier. The emulsifiers are chosen in an appropriate manner according to the emulsion to be obtained. In some cases, the one or more emulsifiers may be selected from the group consisting polygylcerol esters of fatty acids, alkyl polyglycosides, polysorbates, amino acid emulsifiers, and an alkyl amine oxides. Further, in some cases the microemulsion include at least one polyglycerol ester of fatty acids, which has the following formula:

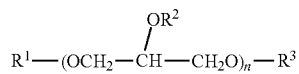

wherein the average value of n is about 3 and R$^1$, R$^2$ and R$^3$ each may independently be a fatty acid moiety or hydrogen, provided that at least one of R$^1$, R$^2$, and R$^3$ is a fatty acid moiety. Non-limiting examples include glyceryl monomyristate, glyceryl monopalmitate, glyceryl monostearate, glyceryl isostearate, glyceryl monooleate, glyceryl ester of mono(olive oil fatty acid), glyceryl dioleate and glyceryl distearate. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and a mixture thereof.

The one or more emulsifiers may include one or more amino acid emulsifiers. In particular, the amino acid emulsifiers include those derived from taurate, glutamate, alanin or alaninate, sarcosinate and aspartate. Amino acid emulsifiers typically have the following structure:

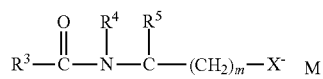

wherein R$^3$ is a saturated or unsaturated, straight or branched alkyl chain with 7 to 17 C atoms, R$^4$ is H or a methyl, R$^5$ is H, COO$^-$M$^+$, CH$^2$COO$^-$M or COOH, m is 0 to 2, X is COO$^-$ or SO$_3^-$ and M is independently H, sodium, potassium or ammonium. In some instances, R$^3$ is a saturated or unsaturated, straight or branched alkyl chain with 9 to 17 C atoms, or 9 to 13 C atoms, R$^4$ is H or a methyl, R$^5$ is H, COO$^-$ M$^+$, CH$_2$COO M or COOH, m is 0 to 2, X is COO$^-$ or SO$_3^-$ and M is independently H, sodium or potassium Non-limiting examples of amino acid emulsifiers include potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, cocoyl methyl β-alanine, lauroyl β-alanine, lauroyl methyl β-alanine, myristoyl β-alanine, potassium lauroyl methyl β-alanine, sodium cocoyl alaninate, sodium cocoyl methyl β-alanine and sodium myristoyl methyl β-alanine palmitoyl glycine, sodium lauroyl glycine, sodium cocoyl glycine, sodium myristoyl glycine, potassium lauroyl glycine, potassium cocoyl glycine, potassium lauroyl sarcosinate, potassium cocoyl sarcosinate, sodium cocoyl sarcosinate, sodium lauroyl sarcosinate, sodium myristoyl sarcosinate, and sodium palmitoyl sarcosinate and mixtures thereof.

Particular mention may be made of potassium lauroyl sarcosinate, potassium cocoyl sarcosinate, sodium cocoyl sarcosinate, sodium lauroyl sarcosinate, sodium lauroyl aspartate, sodium myristoyl aspartate, sodium cocoyl aspartate, sodium caproyl aspartate, disodium lauroyl aspartate, disodium myristoyl aspartate, disodium cocoyl aspartate, disodium caproyl aspartate, potassium lauroyl aspartate, potassium myristoyl aspartate, potassium cocoyl aspartate, potassium caproyl aspartate, dipotassium lauroyl aspartate, dipotassium myristoyl aspartate, dipotassium cocoyl aspartate, dipotassium caproyl aspartate, and mixtures thereof.

Further, non-limiting examples of emulsifiers that may be mentioned include nonionic emulsifiers such as oxyalkylenated (more particularly polyoxyethylenated); oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

In some instance, the one or more emulsifiers include an oganosiloxane emulsifier, including crosslinked organosiloxane emulsifiers. For example, the compositions may comprise one or more crosslinked organosiloxane emulsifier selected from the group consisting of dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer.

In some instances, the microemulsion compositions include one or more linear organosiloxane emulsifier selected from the group consisting of cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone.

Usable oxyalkylenated organosiloxane emulsifier include the following:

An oxyalkylenated organosiloxane emulsifier having the general formula:

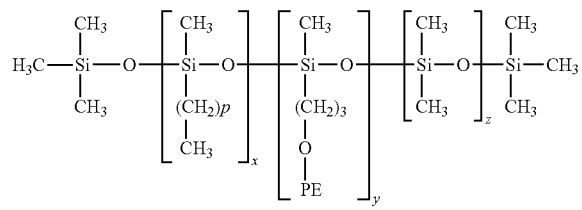

wherein p is 0-40 (the range including all numbers between and subranges such as 2, 3, 4, 13, 14, 15, 16, 17, 18, etc.), and PE is $(\!-\!C_2H_{40}\!-\!)_a(\!-\!C_3H_{60}\!-\!)_b\!-\!H$ wherein a is 0-25, b is 0-25 with the proviso that both a and b cannot be 0 simultaneously, x, y, and z are each independently ranging from 0 to 1 million with the proviso that x and y cannot be 0 simultaneously. In some cases, x, y, z, a, and b are such that the molecular weight of the polymer ranges from about 5,000 to about 500,000, from about 10,000 to 100,000, or is about 50,000, and the polymer is generically referred to as dimethicone copolyol. In some instances, p is such that the long chain alkyl is cetyl or lauryl, and the compound is called, generically, cetyl dimethicone copolyol or lauryl dimethicone copolyol respectively. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

An oxyalkylenated organosiloxane emulsifier having the general formula:

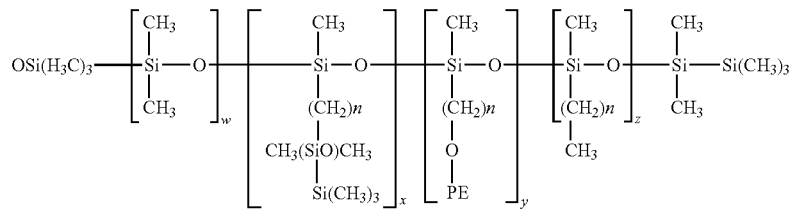

wherein each n is independently 0-100 with the proviso that there must be at least one PE radical. In some instances, where each n independently ranges from about 2 to 30, and PE (—$C_2H_{4O}$)$_a$—(—$C_3H_{6O}$)$_b$—H wherein a is 0-25, b is 0-25 with the proviso that both a and b cannot simultaneously be 0; and wherein w, x, y, and z are each independently 0 to 1,000,000 with the proviso that there is at least one PE. In some cases the organosiloxane emulsifier is lauryl PEG-9 Polydimethylsiloxyethyl Dimethicone. Oxyalkylenated organosiloxane emulsifiers disclosed in U.S. Pat. No. 9,095,543 are useful in the instant compositions. U.S. Pat. No. 9,095,543 is incorporated herein by reference in its entirety.

Further examples of organosiloxane emulsifiers include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; or mixtures thereof.

Further examples of commercial linear organosiloxane emulsifiers are those sold by Dow Corning under the tradename Dow Corning 322° C. Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of fully or partially cross-linked oxyalkylenated organosiloxane emulsifiers. They may be elastomeric or non-elastomeric. They are sometimes referred to as "emulsifying elastomers" because of they have both elastomeric and emulsifying properties.

Polyoxyalkylenated silicone elastomers that may be used include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers include dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

Further examples of crosslinked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 Dimethicone/Vinyl Dimethicone Crosspolymer; PEG-10 Lauryl Dimethicone Crosspolymer; PEG-15/Lauryl Dimethicone Crosspolymer; and PEG-15 Laurylpolydimethylsiloxyethyl Crosspolymer.

Cosmetically Acceptable Carrier

The cosmetically acceptable carrier can include, for example, glycerin, $C_{1-4}$alcohols, organic solvents, fatty alcohols, fatty ethers, fatty esters, polyols, glycols, vegetable oils, mineral oils, liposomes, laminar lipid materials, water, or any combinations thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof.

Auxiliary Ingredients

The compositions according to the disclosure may further comprise any auxiliary ingredient selected, for example, from conditioning agents, natural and synthetic oils, humectants, shine agents, fillers, colorants, pigments, chelating agents, sequestering agents, fragrances, preservatives, stabilizers, and mixtures thereof.

The amount of auxiliary ingredient depends partly on the nature of the ingredient. In some case, the amount of the auxiliary ingredient may be about 0.1 wt. % to about 30 wt. %, about 0.1 wt. % to about 20 wt. %, about 0.1 wt. % to about 15 wt. %, about 0.1 wt. % to about 10 wt. %, 0.1 wt. % to about 5 wt. %, about 0.1 wt. % to about 3 wt. %, or about 0.1 wt. % to about 2 wt. %.

In some cases, the hair care compositions are in the form of a gel, paste, or cream, and have a viscosity of from about 405 to about 490 cps or mPa·s, about 420 to about 475 cps or mPa·s, about 420 to about 450 cps or mPa·s, about 405 to about 450 cps or mPa·s, as measured by, for example, a Brookfield rheometer at 25° C.

EXAMPLES

The following Examples are intended to be non-restrictive and explanatory only, with the scope of the invention being defined by the claims. The ingredient amounts in the compositions/formulas described below are expressed in % by weight, based on the total weight of the composition/formula.

Example 1

Ionic Liquid

Thiolactic acid was added to ice cooled triethanolamine (TEA) such that the ratio of TLA to TEA was about 1:1 (mole ratio). After 24 hours of mixing, water was removed from the mixture by rotatory evaporation and the residue washed with diethylether. The washed residue was subjected to rotatory evaporation again for 3 hours at 40° C. The resulting residue was an ionic liquid in the form of viscous oil.

Example 2

Ionic Liquid

Thiolactic acid was added to an ice cooled choline hydroxide such that the ratio of thiolactic acid to choline hydroxide was about 1:1 (mole ratio). After 24 hours of mixing, water was removed from the mixture by rotatory evaporation and the residue washed with diethylether. The washed residue was subjected to rotatory evaporation again, for 3 hours at 40° C. The resulting residue was an ionic liquid in the form of viscous oil.

Example 3

Hair Care Composition (Gel)

The ionic liquid of Example 1 can be formulated as a hair care composition (gel), as shown below.

| INCI US | Wt. % |
|---|---|
| IONIC LIQUID FORMED FROM THIOLACTIC ACID (TLA) & TRIETHANOLAMINE (TEA) (1:1 Molar Ratio) | 8 |
| HYDROXYETHYLCELLULOSE CELLULOSE PCG-10 (AMERCHOL/DOW CHEMICAL) | 0.75 |
| PEG-12 DIMETHICONE | 2 |
| WATER | Q.S. 100 |

The gel can be prepared by heating the water to about 70° C. and then adding the cellulose material or other thickening agents. While keeping the temperature at about 70° C. continue mixing for about 30 minutes. After mixing for about 30 minutes, add the silicone material and mix for an additional 15 minutes at 70° C. Then cool the mixture to 25° C. Adjust the pH if desired and check the viscosity. The viscosity can be measured using various viscometers and rheometer types, for example, the Mettler RM 180 Rheomat, viscometer spindle #2, at 25° C. (uD=Units of Deflection) or Brookfield rheometers, which are used in the art.

A gel texture provides the benefits of ease of application of the hair care composition into the hair, spreadability of the composition on the hair, and/or ease of brushing or combing the hair. A hair care composition with a gel texture does not readily drip off the hair contacted with the composition and remains on the hair during treatment, for example, during the straightening processing time. The consistency and texture of the hair care composition allows it to be packaged jars, in tubes (e.g., squeeze tubes) or bottles (e.g., applicator bottles).

The stability of the hair care composition can be measured by placing the composition in a humidity-controlled environment set at 4° C., 25° C. and 45° C. for at least 2 months. A composition is considered to be stable when there are very little fluctuations in viscosity and pH.

Example 4

Hair Care Composition (Gel)

The ionic liquid of Example 2 can be formulated as a hair care composition (gel), as shown below.

| INCI US | Wt. % |
|---|---|
| IONIC LIQUID FROM THIOLACTIC ACID (TLA) & CHOLINE HYDROXIDE (1:1 Molar Ratio) | 8 |
| HYDROXYETHYLCELLULOSE CELLULOSE PCG-10 (AMERCHOL/DOW CHEMICAL) | 0.75 |
| PEG-12 DIMETHICONE | 2 |
| WATER | Q.S.100 |

The gel of Example 4 can be prepared and tested in the same manner as the gel of Example 3 (above).

Example 5

Hair Care Composition (Kit)

The components of the gels of Examples 3 and 4 may be provided in a kit having two (or more) parts, as shown below.

| GEL COMPONENT A | Wt. % |
|---|---|
| HYDROXYETHYLCELLULOSE | 0.75 |
| CELLULOSE PCG-10 (AMERCHOL/DOW CHEMICAL) | |
| PEG-12 DIMETHICONE | 2 |
| WATER | Q.S.100 |

| IONIC LIQUID COMPONENT B | Wt. % |
|---|---|
| IONIC LIQUID FORMED FROM THIOLACTIC ACID (TLA) & TRIETHANOLAMINE (TEA)(1:1 Molar Ratio) OR FROM TLA AND CHOLINE HYDROXIDE (1:1 Molar Ratio) | 8 |

Ionic liquid component B is added to gel component A immediately before use to form a ready-to-use hair care composition. The ready-to-use hair care composition can be applied to the hair, for example, within one or two hours after mixing ionic liquid component B with gel component A.

Example 6

Aqueous Shampoos

Aqueous shampoos comprising different types of surfactants and amounts of surfactants can be prepared in water according to the table below.

| Ingredient | % by Weight (active matter, "AM") |
|---|---|
| Anionic surfactants (eg, sodium laureth sulfate, sodium lauryl sulfate, sodium lauroyl sarcosinate, disodium laureth sulfosuccinate, sodium lauryl sulfoacetate, sodium cocoyl isethionate, or mixtures thereof) | 5-20 |
| Amphoteric surfactants (eg, coco betaine, cocamidopropylbetaine, cocoamphoacetate, cocoamphodiacetate, and their salts, or mixtures thereof) | 0.1-10 |
| Ionic liquid formed from thiolactic acid (TLA) & triethanolamine (TEA) (1:1 Molar Ratio) or ionic liquid formed from TLA & choline hydroxide (1:1 Molar Ratio) | 0.5-15 |
| Thickening agents (e.g., guar hydroxypropyltrimonium chloride, carbomer, hydroxyethylcellulose) | 0.01-2 |
| Nonionic surfactants (e.g., glyceryl esters, fatty alcohols, alkoxylated alcohols, alkylpolglucosides, or mixtures thereof) | 0.01-10 |
| Cationic conditioning polymers compounds (e.g., quaternary ammonium compounds such as polyquaternium compounds) | 0.01-4 |
| Silicones (eg, amodimethicone, divinyl dimethicone/dimethicone copolymer, dimethicone, or mixtures thereof) | 0-10 |
| Water, organic solvent, and additional components such as plant/vegetable oils, hydrocarbons, lower alkanes, fragrance, preservatives, pH adjusters, extracts, salts, vitamins, sunscreens, colorants (as needed or desired) | Q.S. 100 |

Example 6(a)

Hair Care Compositions (Sulfate-Based Shampoos)

| US INCI NAME | Ex. A | Ex B | Ex. C | Ex. D |
|---|---|---|---|---|
| | \multicolumn{4}{c}{% by wt} | | | |
| SODIUM LAURETH SULFATE | 17.6 | 17.6 | 17.6 | 17.6 |
| DISODIUM COCOAMPHODIACETATE | 1.61 | 1.61 | 1.61 | 1.61 |
| COCO-BETAINE | 4.4 | 4.4 | 4.4 | 4.4 |
| COCAMIDE MIPA | 0.7 | 0.7 | 0.7 | 0.7 |
| IONIC LIQUID FORMED FROM THIOLACTIC ACID (TLA) & TRIETHANOLAMINE (TEA) (1:1 MOLAR RATIO) OR FORMED FROM TLA & CHOLINE HYDROXIDE (1:1 MOLAR RATIO) | 2 | 5 | 10 | 16 |
| CARBOMER | 0.15 | 0.15 | 0.15 | 0.15 |
| GUAR HYDROXYPROPYLTRIMONIUM CHLORIDE | 0.2 | 0.2 | 0.2 | 0.2 |
| GLYCOL DISTEARATE | 1.61 | 1.61 | 1.61 | 1.61 |
| DIMETHICONE | 1.88 | 1.88 | 1.88 | 1.88 |
| *THEOBROMA CACAO* (COCOA) SEED BUTTER | 0.01 | 0.01 | 0.01 | 0.01 |

-continued

| US INCI NAME | Ex. A | Ex B | Ex. C | Ex. D |
|---|---|---|---|---|
| | | % by wt | | |
| ADDITIONAL COMPONENTS (E.G., ORGANIC SOLVENT, PRESERVATIVES, PH ADJUSTING AGENTS, PLANT EXTRACTS, HYDROLYZED PROTEINS VITAMINS, SALT, AND FRAGRANCES) | 2.2 | 2.2 | 2.2 | 2.2 |
| WATER QS | 100 | 100 | 100 | 100 |

Example 6(b)

Hair Care Compositions (Sulfate-Free Shampoos)

| US INCI NAME | Ex. E | Ex. F | Ex. G | Ex. H |
|---|---|---|---|---|
| | | % by wt | | |
| SODIUM LAUROYL SARCOSINATE | 7.2 | 7.2 | 7.2 | 7.2 |
| DISODIUM LAURETH SULFOSUCCINATE (and) SODIUM LAURYL SULFOACETATE | 40.5 | 40.5 | 40.5 | 40.5 |
| SODIUM COCOYL ISETHIONATE | 9 | 9 | 9 | 9 |
| COCAMIDOPROPYL BETAINE | 4.74 | 4.74 | 4.74 | 4.74 |
| IONIC LIQUID FORMED FROM THIOLACTIC ACID (TLA) & TRIETHANOLAMINE (TEA) (1:1 MOLAR RATIO) OR FORMED FROM TLA & CHOLINE HYDROXIDE (1:1 MOLAR RATIO) | 2 | 5 | 10 | 16 |
| CARBOMER | 0.2 | 0.2 | 0.2 | 0.2 |
| DECYL GLUCOSIDE | 0.93 | 0.93 | 0.93 | 0.93 |
| PROPYLENE GLYCOL (and) PEG-55 PROPYLENE GLYCOL OLEATE (ester) | 0.7 | 0.7 | 0.7 | 0.7 |
| PPG-5-CETETH-20 | 0.5 | 0.5 | 0.5 | 0.5 |
| GLYCOL DISTEARATE | 1.8 | 1.8 | 1.8 | 1.8 |
| POLYQUATERNIUM-10 | 0.3 (0.273% AM) | 0.3 (0.273% AM) | 0.3 (0.273% AM) | 0.3 (0.273% AM) |
| POLYQUATERNIUM-7 | 4.44 (0.4% AM) | 4.44 (0.4% AM) | 4.44 (0.4% AM) | 4.44 (0.4% AM) |
| DIVINYLDIMETHICONE/DIMETHICONE COPOLYMER | 0.45 | 0.45 | 0.45 | 0.45 |
| AMODIMETHICONE | 0.4 | 0.4 | 0.4 | 0.4 |
| C12-13 PARETH-3 | 0.016 | 0.016 | 0.016 | 0.016 |
| C12-13 PARETH-23 | 0.016 | 0.016 | 0.016 | 0.016 |
| C11-15 PARETH-7 | 0.16 | 0.16 | 0.16 | 0.16 |
| LAURETH-9 | 0.08 | 0.08 | 0.08 | 0.08 |
| TRIDECETH-12 | 0.04 | 0.04 | 0.04 | 0.04 |
| ADDITIONAL COMPONENTS (E.G., PRESERVATIVES, PH ADJUSTING AGENTS, PLANT EXTRACTS, PLANT OILS, HYDROLYZED PROTEINS VITAMINS, SALT, AND FRAGRANCES) | 2.11 | 2.11 | 2.11 | 2.11 |
| WATER QS | 100 | 100 | 100 | 100 |

Example 7

Rinse Off Conditioner, Masks, and Leave-on Product

Rinse off conditioners, masques, and leave-on products comprising different types of surfactants and amounts of surfactants can be prepared in water according to the table below.

| Ingredient | % by Weight (active matter, "AM") |
|---|---|
| Cationic surfactants (e.g., cetrimonium chloride, behentrimonium chloride, and mixtures thereof) | 0.1-10 |
| Ionic liquid formed from thiolactic acid (TLA) & triethanolamine (TEA) (1:1 Molar Ratio) or formed from TLA & choline hydroxide (1:1 Molar Ratio) | 1-30 |
| Fatty alcohols (e.g., cetearyl alcohol, cetyl alcohol, steary alcohol, and mixtures thereof) | 0.1-20 |
| Fatty compounds other than fatty alcohols | 0-10 |
| Starch derivative | 0-10 |
| Amino Silicones (eg, amodimethicone) | 0.01-10 |
| Cationic conditioning polymers compounds (e.g., quaternary ammonium compounds such as polyquaternium compounds) | 0-4 |
| Water, organic solvent, and additional components such as non-amino silicones, non-polymeric conditioning agents, plant/vegetable oils, thickening agents, nonionic surfactants other than fatty alcohols, hydrocarbons, lower alkanes, fragrance, preservatives, pH adjusters, plant extracts, salts, vitamins, sunscreens, colorants (as needed or desired) | Q.S. 100 |

Example 8 (a)

Rinse-Off Conditioners

| US INCI NAME | Ex. A | Ex. B | Ex. C | Ex. D |
|---|---|---|---|---|
| | | % by wt | | |
| IONIC LIQUID FORMED FROM THIOLACTIC ACID (TLA) & TRIETHANOLAMINE (TEA) (1:1 MOLAR RATIO) OR FORMED FROM TLA & CHOLINE HYDROXIDE (1:1 MOLAR RATIO) | 2 | 5 | 10 | 16 |
| BEHENTRIMONIUM CHLORIDE | 2.37 | 2.37 | 2.37 | 2.37 |
| CETEARYL ALCOHOL | 7 | 7 | 7 | 7 |
| GLYCERIN | 0.5 | 0.5 | 0.5 | 0.5 |
| SYNTHETIC FLUORPHLOGOPITE (and) TITANIUM DIOXIDE | 3 | 3 | 3 | 3 |
| WATER AND ADDITIONAL COMPONENT (PRESERVATIVES) QS | 100 | 100 | 100 | 100 |

Example 8 (b)

Rinse-Off Conditioner Masks

| US INCI NAME | Ex. E | Ex. F | Ex. G | Ex. H |
|---|---|---|---|---|
| | | % by weight | | |
| IONIC LIQUID FORMED FROM THIOLACTIC ACID (TLA) & TRIETHANOLAMINE (TEA) (1:1 MOLAR RATIO) OR FORMED FROM TLA & CHOLINE HYDROXIDE (1:1 MOLAR RATIO) | 2 | 5 | 10 | 16 |
| CETTRIMONIUM CHLORIDE | 0.8 | 0.8 | 0.8 | 0.8 |
| DIPALMITOYLETHYL HYDROXYETHYLMONIUM METHOSULFATE | 1.35 | 1.35 | 1.35 | 1.35 |
| CETEARYL ALCOHOL | 9.15 | 9.15 | 9.15 | 9.15 |
| CETYL ESTERS (and) CETYL ESTERS | 1 | 1 | 1 | 1 |
| MINERAL OIL | 2 | 2 | 2 | 2 |
| WATER AND ADDITIONAL COMPONENT (PRESERVATIVES) QS | 100 | 100 | 100 | 100 |

Example 8 (c)

Leave-On Products

| US INCI NAME | Ex. I | Ex. J | Ex. K | Ex. L |
|---|---|---|---|---|
| | | % by weight | | |
| IONIC LIQUID FORMED FROM THIOLACTIC ACID (TLA) & TRIETHANOLAMINE (TEA) (1:1 MOLAR RATIO) OR FORMED FROM TLA & CHOLINE HYDROXIDE (1:1 MOLAR RATIO) | 2 | 5 | 10 | 16 |
| CETRIMONIUM CHLORIDE | 1.5 | 1.5 | 1.5 | 1.5 |
| DIPALMITOYLETHYL HYDROXYETHYLMONIUM METHOSULFATE | 0.98 | 0.98 | 0.98 | 0.98 |
| CETEARYL ALCOHOL | 4.8 | 4.8 | 4.8 | 4.8 |
| GUAR HYDROXYPROPYL-TRIMONIUM CHLORIDE | 0.25 | 0.25 | 0.25 | 0.25 |
| HYDROXYPROPYL-TRIMONIUM HYDROLYZED WHEAT PROTEIN | 0.05 | 0.05 | 0.05 | 0.05 |
| MINERAL OIL | 1.5 | 1.5 | 1.5 | 1.5 |
| DIMETHICONE | 1 | 1 | 1 | 1 |
| GLYCERIN | 0.5 | 0.5 | 0.5 | 0.5 |
| AMINO ACIDS | 0.075 | 0.075 | 0.075 | 0.075 |
| CAPRYLOYL GLYCINE | 0.01 | 0.01 | 0.01 | 0.01 |
| WATER AND ADDITIONAL COMPONENT (PRESERVATIVES, NEUTRALIZING AGENT) QS | 100 | 100 | 100 | 100 |

Example 9

Ionic Mixture

Thiolactic acid was added to ice cooled triethanolamine (TEA) such that the ratio of TLA to TEA was about 1:1 (mole ratio). The resulting residue was an ionic mixture in the form of viscous liquid. No further processing was required to derive the ionic mixture. Unlike the ionic liquids in Examples 1 and 2, the the resulting residue of the ionic mixture in the instant case does not require removal of water (e.g., rotary evaporation and washing with diethylether is not needed). A similar process may be used to make ionic mixtures with different molar ratios, for example, mixtures having an excess of TLA component to TEA component (e.g., 2:1 molar ratio).

Example 10

Ionic Mixture

Thiolactic acid was added to ice cooled choline hydroxide such that the ratio of thiolactic acid to choline was about 1:1 (mole ratio). The resulting residue was an ionic mixture in the form of viscous liquid. Unlike the ionic liquids in Examples 1 and 2, the the resulting residue of the ionic mixture in the instant case does not require removal of water (e.g., rotary evaporation and washing with diethylether is not needed). A similar process may be used to make ionic mixtures with different molar ratios, for example, mixtures having an excess of TLA component to choline component (e.g., 2:1 molar ratio).

Example 11

Hair Care Composition (Gel)

The ionic mixture of Example 9 can be formulated as a hair care composition (gel), as shown below.

| INCI US | Wt. % |
| --- | --- |
| IONIC MIXTURE OF THIOLACTIC ACID (TLA) & TRIETHANOLAMINE (TEA) | 8 |
| HYDROXYETHYLCELLULOSE CELLULOSE PCG-10 (AMERCHOL/DOW CHEMICAL) | 0.75 |
| PEG-12 DIMETHICONE | 2 |
| WATER | Q.S. 100 |

The gel can be prepared by heating the water to about 70° C. and then adding the cellulose material or other thickening agents. While keeping the temperature at about 70° C. continue mixing for about 30 minutes. After mixing for about 30 minutes, add the silicone material and mix for an additional 15 minutes at 70° C. Then cool the mixture to 25° C. Adjust the pH if desired and check the viscosity. The viscosity can be measured using various viscometers and rheometer types, for example, the Mettler RM 180 Rheomat, viscometer spindle #2, at 25° C. (uD=Units of Deflection).

A Rheomat viscosity measurement in M2 units ranging up from about 60 to 65 M2 generally corresponds to a texture and consistency of a gel composition. A gel texture provides the benefits of ease of application of the hair care composition into the hair, spreadability of the composition on the hair, and/or ease of brushing or combing the hair. A hair care composition with a gel texture does not readily drip off the hair contacted with the composition and remains on the hair during treatment, for example, during the straightening processing time. The consistency and texture of the hair care composition allows it to be packaged jars, in tubes (e.g., squeeze tubes) or bottles (e.g., applicator bottles).

The stability of the hair care composition can be measured by placing the composition in a humidity-controlled environment set at 4° C., 25° C. and 45° C. for at least 2 months. A composition is considered to be stable when there are very little fluctuations in viscosity and pH.

Example 12

Hair Care Composition (Gel)

The ionic mixture of Example 10 can be formulated as a hair care composition (gel), as shown below.

| INCI US | Wt. % |
| --- | --- |
| IONIC MIXTURE OF THIOLACTIC ACID (TLA) & CHOLINE HYDROXIDE | 8 |
| HYDROXYETHYLCELLULOSE CELLULOSE PCG-10 (AMERCHOL/DOW CHEMICAL) | 0.75 |
| PEG-12 DIMETHICONE | 2 |
| WATER | Q.S.100 |

The gel of Example 12 can be prepared and tested in the same manner as the gel of Example 11 (above).

Example 13

Hair Care Composition (Kit)

The components of the gels of Examples 11 and 12 may be provided in a kit having two (or more) parts, as shown below.

| GEL COMPONENT A | Wt. % |
| --- | --- |
| HYDROXYETHYLCELLULOSE CELLULOSE PCG-10 (AMERCHOL/DOW CHEMICAL) | 0.75 |
| PEG-12 DIMETHICONE | 2 |
| WATER | Q.S.100 |

| IONIC MIXTURE COMPONENT B | Wt. % |
| --- | --- |
| IONIC MIXTURE OF THIOLACTIC ACID (TLA) & TRIETHANOLAMINE (TEA) (1:1 Molar Ratio) OR IONIC MIXTURE OF TLA AND CHOLINE HYROXIDE | 8 |

Ionic mixture component B is added to gel component A immediately before use to form a ready-to-use hair care composition. The ready-to-use hair care composition can be applied to the hair, for example, within one or two hours after mixing ionic mixture component B with gel component A.

Example 14

Aqueous Shampoos

Aqueous shampoos comprising different types of surfactants and amounts of surfactants can be prepared in water according to the table below.

| Ingredient | % by Weight (active matter, "AM") |
|---|---|
| Anionic surfactants (eg, sodium laureth sulfate, sodium lauryl sulfate, sodium lauroyl sarcosinate, disodium laureth sulfosuccinate, sodium lauryl sulfoacetate, sodium cocoyl isethionate, or mixtures thereof) | 5-20 |
| Amphoteric surfactants (eg, coco betaine, cocamidopropylbetaine, cocoamphoacetate, cocoamphodiacetate, and their salts, or mixtures thereof) | 0.1-10 |
| Ionic mixture of thiolactic acid (TLA) & triethanolamine (TEA) or ionic mixture of TLA & choline hydroxide | 0.5-15 |
| Thickening agents (e.g., guar hydroxypropyltrimonium chloride, carbomer, hydroxyethylcellulose) | 0.01-2 |
| Nonionic surfactants (e.g., glyceryl esters, fatty alcohols, alkoxylated alcohols, alkylpolglucosides, or mixtures thereof) | 0.01-10 |
| Cationic conditioning polymers compounds (e.g., quaternary ammonium compounds such as polyquaternium compounds) | 0.01-4 |
| Silicones (eg, amodimethicone, divinyl dimethicone/dimethicone copolymer, dimethicone, or mixtures thereof) | 0-10 |
| Water, organic solvent, and additional components such as plant/vegetable oils, hydrocarbons, lower alkanes, fragrance, preservatives, pH adjusters, extracts, salts, vitamins, sunscreens, colorants (as needed or desired) | Q.S. 100 |

Example 15(a)

Hair Care Compositions (Sulfate-Based Shampoos)

| US INCI NAME | Ex. A | Ex B | Ex. C | Ex. D |
|---|---|---|---|---|
| | % by wt | | | |
| SODIUM LAURETH SULFATE | 17.6 | 17.6 | 17.6 | 17.6 |
| DISODIUM COCOAMPHODIACETATE | 1.61 | 1.61 | 1.61 | 1.61 |
| COCO-BETAINE | 4.4 | 4.4 | 4.4 | 4.4 |
| COCAMIDE MIPA | 0.7 | 0.7 | 0.7 | 0.7 |
| IONIC MIXTURE OF THIOLACTIC ACID (TLA) & TRIETHANOLAMINE (TEA) OR IONIC MIXTURE OF TLA & CHOLINE HYDROXIDE | 2 | 5 | 10 | 16 |
| CARBOMER | 0.15 | 0.15 | 0.15 | 0.15 |
| GUAR HYDROXYPROPYL-TRIMONIUM CHLORIDE | 0.2 | 0.2 | 0.2 | 0.2 |
| GLYCOL DISTEARATE | 1.61 | 1.61 | 1.61 | 1.61 |
| DIMETHICONE | 1.88 | 1.88 | 1.88 | 1.88 |
| *THEOBROMA CACAO* (COCOA) SEED BUTTER | 0.01 | 0.01 | 0.01 | 0.01 |
| ADDITIONAL COMPONENTS (E.G., ORGANIC SOLVENT, PRESERVATIVES, PH ADJUSTING AGENTS, PLANT EXTRACTS, HYDROLYZED PROTEINS VITAMINS, SALT, AND FRAGRANCES) | 2.2 | 2.2 | 2.2 | 2.2 |
| WATER QS | 100 | 100 | 100 | 100 |

Example 15(b)

Hair Care Compositions (Sulfate-Free Shampoos)

| US INCI NAME | Ex. E | Ex. F | Ex. G | Ex. H |
|---|---|---|---|---|
| | % by wt | | | |
| SODIUM LAUROYL SARCOSINATE | 7.2 | 7.2 | 7.2 | 7.2 |
| DISODIUM LAURETH SULFOSUCCINATE (and) SODIUM LAURYL SULFOACETATE | 40.5 | 40.5 | 40.5 | 40.5 |
| SODIUM COCOYL ISETHIONATE | 9 | 9 | 9 | 9 |
| COCAMIDOPROPYL BETAINE | 4.74 | 4.74 | 4.74 | 4.74 |
| IONIC MIXTURE OF THIOLACTIC ACID (TLA) & TRIETHANOLAMINE (TEA) OR IONIC MIXTURE OF TLA & CHOLINE HYDROXIDE | 2 | 5 | 10 | 16 |
| CARBOMER | 0.2 | 0.2 | 0.2 | 0.2 |
| DECYL GLUCOSIDE | 0.93 | 0.93 | 0.93 | 0.93 |
| PROPYLENE GLYCOL (and) PEG-55 PROPYLENE GLYCOL OLEATE (ester) | 0.7 | 0.7 | 0.7 | 0.7 |
| PPG-5-CETETH-20 | 0.5 | 0.5 | 0.5 | 0.5 |
| GLYCOL DISTEARATE | 1.8 | 1.8 | 1.8 | 1.8 |
| POLYQUATERNIUM-10 | 0.3 (0.273% AM) | 0.3 (0.273% AM) | 0.3 (0.273% AM) | 0.3 (0.273% AM) |
| POLYQUATERNIUM-7 | 4.44 (0.4% AM) | 4.44 (0.4% AM) | 4.44 (0.4% AM) | 4.44 (0.4% AM) |
| DIVINYLDIMETHICONE/DIMETHICONE COPOLYMER | 0.45 | 0.45 | 0.45 | 0.45 |
| AMODIMETHICONE | 0.4 | 0.4 | 0.4 | 0.4 |
| C12-13 PARETH-3 | 0.016 | 0.016 | 0.016 | 0.016 |
| C12-13 PARETH-23 | 0.016 | 0.016 | 0.016 | 0.016 |
| C11-15 PARETH-7 | 0.16 | 0.16 | 0.16 | 0.16 |
| LAURETH-9 | 0.08 | 0.08 | 0.08 | 0.08 |
| TRIDECETH-12 | 0.04 | 0.04 | 0.04 | 0.04 |

-continued

| US INCI NAME | Ex. E | Ex. F | Ex. G | Ex. H |
|---|---|---|---|---|
| | % by wt | | | |
| ADDITIONAL COMPONENTS (E.G., PRESERVATIVES, PH ADJUSTING AGENTS, PLANT EXTRACTS, PLANT OILS, HYDROLYZED PROTEINS VITAMINS, SALT, AND FRAGRANCES) | 2.11 | 2.11 | 2.11 | 2.11 |
| WATER QS | 100 | 100 | 100 | 100 |
| pH | 3.5 | 3.5 | 3.5 | 3.5 |

Example 16

Rinse Off Conditioner, Masks, and Leave-on Product

Rinse off conditioners, masques, and leave-on products comprising different types of surfactants and amounts of surfactants can be prepared in water according to the table below.

| Ingredient | % by Weight (active matter, "AM") |
|---|---|
| Cationic surfactants (e.g., cetrimonium chloride, behentrimonium chloride, and mixtures thereof) | 0.1-10 |
| Ionic mixture of thiolactic acid (TLA) & triethanolamine (TEA) or ionic mixture of TLA & choline hydroxide | 1-30 |
| Fatty alcohols (e.g., cetearyl alcohol, cetyl alcohol, steary alcohol, and mixtures thereof) | 0.1-20 |
| Fatty compounds other than fatty alcohols | 0-10 |
| Starch derivative | 0-10 |
| Amino Silicones (eg, amodimethicone) | 0.01-10 |
| Cationic conditioning polymers compounds (e.g., quaternary ammonium compounds such as polyquaternium compounds) | 0-4 |
| Water, organic solvent, and additional components such as non-amino silicones, non-polymeric conditioning agents, plant/vegetable oils, thickening agents, nonionic surfactants other than fatty alcohols, hydrocarbons, lower alkanes, fragrance, preservatives, pH adjusters, plant extracts, salts, vitamins, sunscreens, colorants (as needed or desired) | Q.S. 100 |

Example 17(a)

Rinse-Off Conditioners

| US INCI NAME | Ex. A | Ex. B | Ex. C | Ex. D |
|---|---|---|---|---|
| | % by wt | | | |
| IONIC MIXTURE OF THIOLACTIC ACID (TLA) & TRIETHANOLAMINE (TEA) OR IONIC MIXTURE OF TLA & CHOLINE HYDROXIDE | 2 | 5 | 10 | 16 |
| BEHENTRIMONIUM CHLORIDE | 2.37 | 2.37 | 2.37 | 2.37 |
| CETEARYL ALCOHOL | 7 | 7 | 7 | 7 |
| GLYCERIN | 0.5 | 0.5 | 0.5 | 0.5 |
| SYNTHETIC FLUORPHLOGOPITE (and) TITANIUM DIOXIDE | 3 | 3 | 3 | 3 |
| WATER AND ADDITIONAL COMPONENT (PRESERVATIVES) QS | 100 | 100 | 100 | 100 |
| pH | 3.5 | 3.5 | 3.5 | 3.5 |

Example 17(b)

Rinse-Off Conditioner Masks

| US INCI NAME | Ex. E | Ex. F | Ex. G | Ex. H |
|---|---|---|---|---|
| | % by weight | | | |
| IONIC MIXTURE OF THIOLACTIC ACID (TLA) & TRIETHANOLAMINE (TEA) OR IONIC MIXTURE OF TLA & CHOLINE HYDROXIDE | 2 | 5 | 10 | 16 |
| CETTRIMONIUM CHLORIDE | 0.8 | 0.8 | 0.8 | 0.8 |
| DIPALMITOYLETHYL HYDROXYETHYLMONIUM METHOSULFATE | 1.35 | 1.35 | 1.35 | 1.35 |
| CETEARYL ALCOHOL | 9.15 | 9.15 | 9.15 | 9.15 |
| CETYL ESTERS (and) CETYL ESTERS | 1 | 1 | 1 | 1 |
| MINERAL OIL | 2 | 2 | 2 | 2 |
| WATER AND ADDITIONAL COMPONENT (PRESERVATIVES) QS | 100 | 100 | 100 | 100 |

Example 17(c)

Leave-On Products

| US INCI NAME | Ex. I | Ex. J | Ex. K | Ex. L |
|---|---|---|---|---|
| | % by weight | | | |
| IONIC MIXTURE OF THIOLACTIC ACID (TLA) & TRIETHANOLAMINE (TEA) OR IONIC MIXTURE OF TLA & CHOLINE HYDROXIDE | 2 | 5 | 10 | 16 |
| CETRIMONIUM CHLORIDE | 1.5 | 1.5 | 1.5 | 1.5 |
| DIPALMITOYLETHYL HYDROXYETHYLMONIUM METHOSULFATE | 0.98 | 0.98 | 0.98 | 0.98 |
| CETEARYL ALCOHOL | 4.8 | 4.8 | 4.8 | 4.8 |
| GUAR HYDROXYPROPYL-TRIMONIUM CHLORIDE | 0.25 | 0.25 | 0.25 | 0.25 |
| HYDROXYPROPYL-TRIMONIUM HYDROLYZED WHEAT PROTEIN | 0.05 | 0.05 | 0.05 | 0.05 |
| MINERAL OIL | 1.5 | 1.5 | 1.5 | 1.5 |
| DIMETHICONE | 1 | 1 | 1 | 1 |
| GLYCERIN | 0.5 | 0.5 | 0.5 | 0.5 |
| AMINO ACIDS | 0.075 | 0.075 | 0.075 | 0.075 |
| CAPRYLOYL GLYCINE | 0.01 | 0.01 | 0.01 | 0.01 |
| WATER AND ADDITIONAL COMPONENT (PRESERVATIVES, NEUTRALIZING AGENT) QS | 100 | 100 | 100 | 100 |
| pH | 3.5 | 3.5 | 3.5 | 3.5 |

Example 18

Method for Straightening Hair

The hair care compositions of the instant disclosure can be used in methods for straightening hair. A method for straightening hair is as follows:
1. the hair is washed with a shampoo (neutral pH);
2. the hair is rinsed with water and towel dried or blown dried;
3. a hair care composition (inventive or comparative) is applied to the hair using an applicator brush device;
4. the hair care composition is allowed to remain on the hair for a period of time, such as from 1 minute to 60 minutes;
5. the hair is brushed with a hair brush using several strokes (e.g., about 20 to about 30 strokes);
6. the hair is smoothed and heated with a flat iron at a temperature ranging from about 50° C.—about 250° C., about 100° C. to about 250° C., about 150° C. to about 250° C., about 160° C. to about 250° C., about 170° C. to about 240° C., or about 190° C. to about 230° C., and using at least 3 strokes (or passes);
7. the hair is washed with a shampoo and/or a conditioner (neutral pH);
8. the hair is rinsed with water (if shampoo is used in step 7, then this rinsing step can optionally, be followed by a step of treating the hair with a conditioner having neutral pH, and then rinsing with water);
9. the shampoo/rinse/optional conditioning/rinse cycle is repeated as many times as desired.

Example 19

Method for Straightening Hair

A method for straightening hair is as follows:
1. the hair is washed with a shampoo (neutral pH);
2. the hair is rinsed with water and towel dried or blown dried;
3. a hair care composition (inventive or comparative) is applied to the hair using an applicator brush device;
4. the hair care composition is allowed to remain on the hair for a period of time, such as from 1 minute to 60 minutes;
5. the hair care composition is rinsed off the hair;
6. the hair is brushed with a hair brush using several strokes (e.g., about 20 to about 30 strokes);
7. the hair is smoothed and heated with a flat iron at a temperature ranging from about 50° C.—about 250° C., about 100° C. to about 250° C., about 150° C. to about 250° C., about 160° C. to about 250° C., about 170° C. to about 240° C., or about 190° C. to about 230° C., and using at least 3 strokes (or passes);
8. the hair is treated with a shampoo and/or a conditioner (neutral pH);
9. the hair is rinsed with water; (if shampoo is used in step 7, then this rinsing step can optionally be followed by a step of treating the hair with a conditioner having a neutral pH, and then rinsing with water);
10. the shampoo/rinse/optional conditioning/rinse cycle is repeated as many times as desired.

Example 20

Assesment of Ionic Liquids

The ionic liquids of Example 1 and Example 2 were combined with water to form compositions comprising 8 wt. % of the ionic liquid. One composition was prepared using 8 wt. % of the ionic liquid formed from thiolactic acid and triethanolamine ("TEA") (Example 1) and another composition was prepared using 8 wt. % of the ionic liquid formed from thiolactic acid and choline hydroxide ("CHO") (Example 2). A third composition was formed using 8 wt. % thiolactic acid alone. Hair swatches were treated according to the methods of Example 5 or Example 6. The fibers of the treated hair were then subjected to a tensile test using an MTT (Miniature Tensile Tester). The wet tensile strength was assessed using the fiber tensile testing instrument Dia-Stron (50 fibers per test). From the test, the following parameters were determined: Young's Modulus (Elasticity, MPa), Break Stress (Force required to break the fiber, MPa) and Break Extension (extent of deformation of the fiber prior to breaking, measured as % of hair length). The hair swatches were also analyzed using Differential Scanning Calorimetry (DSC) (Q-100, TA instruments). The hair swatches were sealed in high pressure pans and heated from 40° C. to 180° C., at a heating rate of 100° C. per minute. At least 3 runs per sample were performed (sample weight 6-7.5 mg). The results were averaged and standard deviation determined. For each sample, cut hair fibers were weighed, 50 µL of water added, and the container was sealed and stored overnight to achieve equilibrium water content and distribution.

A higher Young's modulus and higher break stress represents stronger hair fibers, thereby showing that the hair is less damaged and is more similar to natural hair that has not been subjected to chemical treatment(s). Similarly, higher denaturation temperatures and higher enthalpy also represents stronger hair fibers (stronger hair fibers require more energy to denature the proteins in the hair). Ideally, the Young's modulus, the break stress, the denaturation temperature, and enthalpy of treated hair are similar to the values for natural hair, thereby indicating that the treated hair is not damaged.

Figure 2:
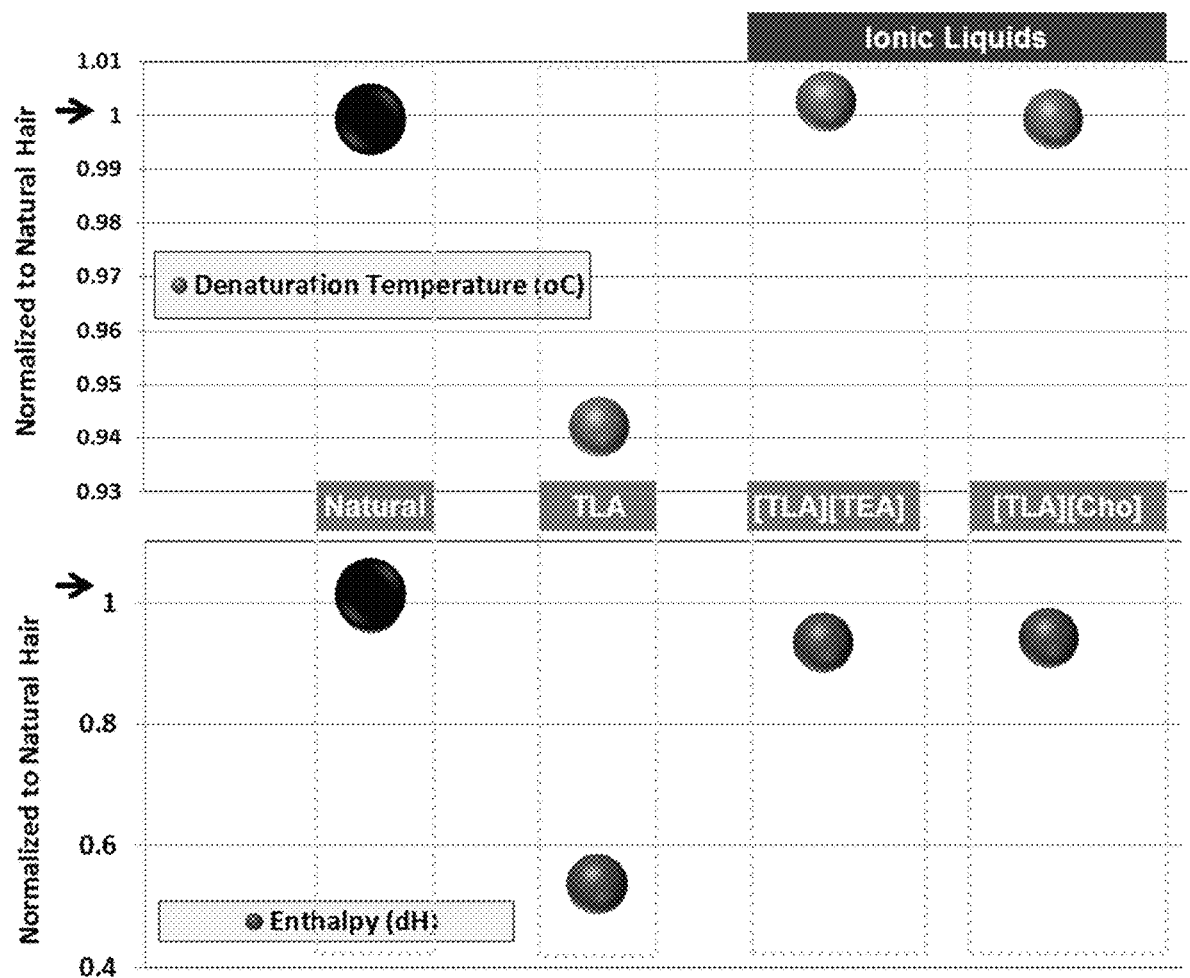
FIG. 2 is a graph showing the denaturation temperature and enthalpy of natural hair, hair treated with thiolactic acid, and hair treated with thiolactic acid-based ionic liquids.

FIG. 1 shows the Young's Modulus, the break test results, and the break extension (%) for natural hair and compares it to the hair treated with thiolactic acid (TLA) alone, and hair treated with each of the ionic liquids. FIG. 2 shows the denaturation temperature and enthalpy of natural hair and compares it to hair treated with thiolactic acid alone, and hair treated with each of the ionic liquids.

Example 21

Assessment of Ionic Mixtures

The ionic mixtures of Example 12 and Example 13 were combined with water to form compositions comprising 8 wt. % of the ionic mixture. One composition was formed using 8 wt. % of the ionic mixture of thiolactic acid and triethanolamine ("TEA") (Example 12) and another composition was formed using 8 wt. % of the ionic mixture of thiolactic acid and choline ("CHO") (Example 13). A third composition was formed using 8 wt. % thiolactic acid alone. Hair swatches were treated according to the methods of Example 5 or Example 6. The treated hair was then subjected to an MTT (Miniature Tensile Test). The wet tensile strength was assessed using the fiber tensile testing instrument Dia-Stron (50 fibers per test). From the test, the following parameters were determined: Young's Modulus (Elasticity, MPa), Break Stress (Force required to break the fiber, MPa) and Break Extension (extent of deformation of the fiber prior to breaking, measured as % of hair length). The hair swatches were also analyzed using Differential Scanning Calorimetry (DSC) (Q-100, TA instruments). The hair swatches were sealed in high pressure pans and heated from 40° C. to 180° C., at a heating rate of 10° C. per minute. At least 3 runs per sample were performed (sample weight 6-7.5 mg). The results were averaged and standard deviation determined. For each sample, cut hair fibers ere weighed, 50 μL of water added, and the container sealed and stored overnight to achieve equilibrium water content and distribution.

Figure 3:
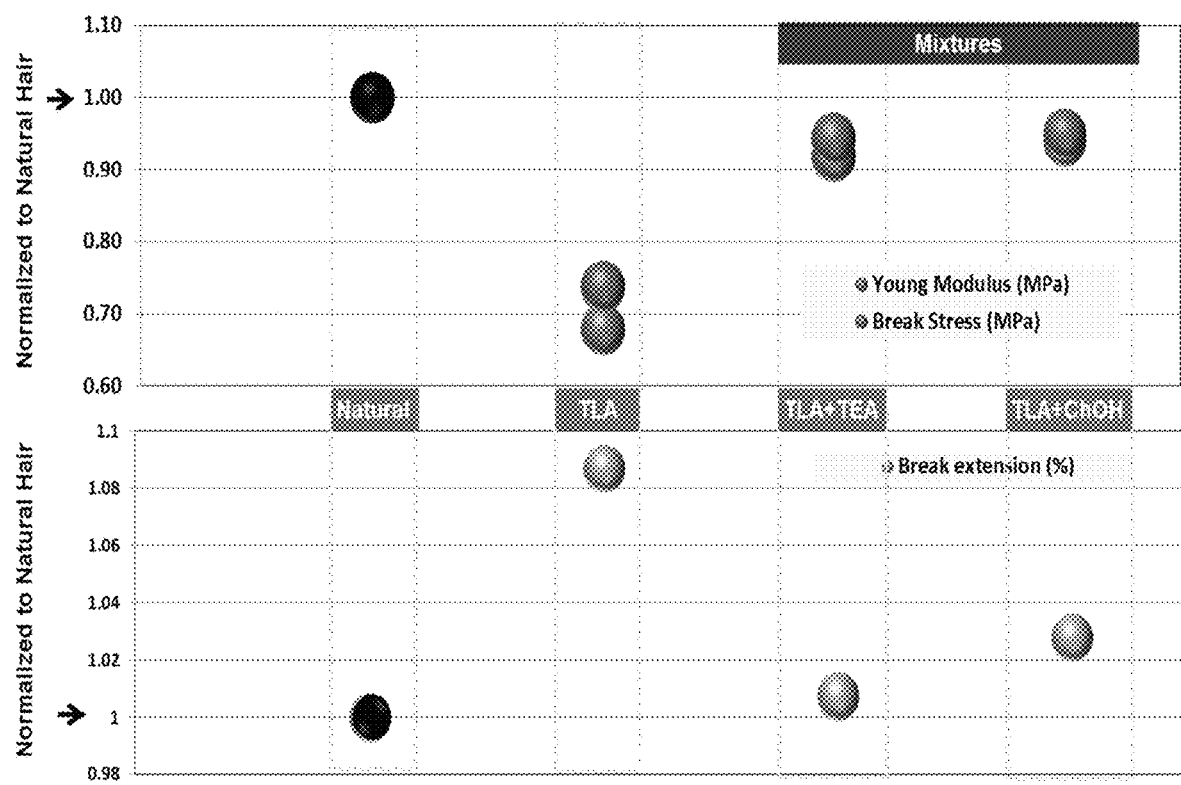
FIG. 3 is a graph showing the Young's Modulus, the break test results, and the break extension (%) for natural hair, hair treated with thiolactic acid (TLA), and hair treated with thiolactic acid-based ionic mixtures.
Figure 4:
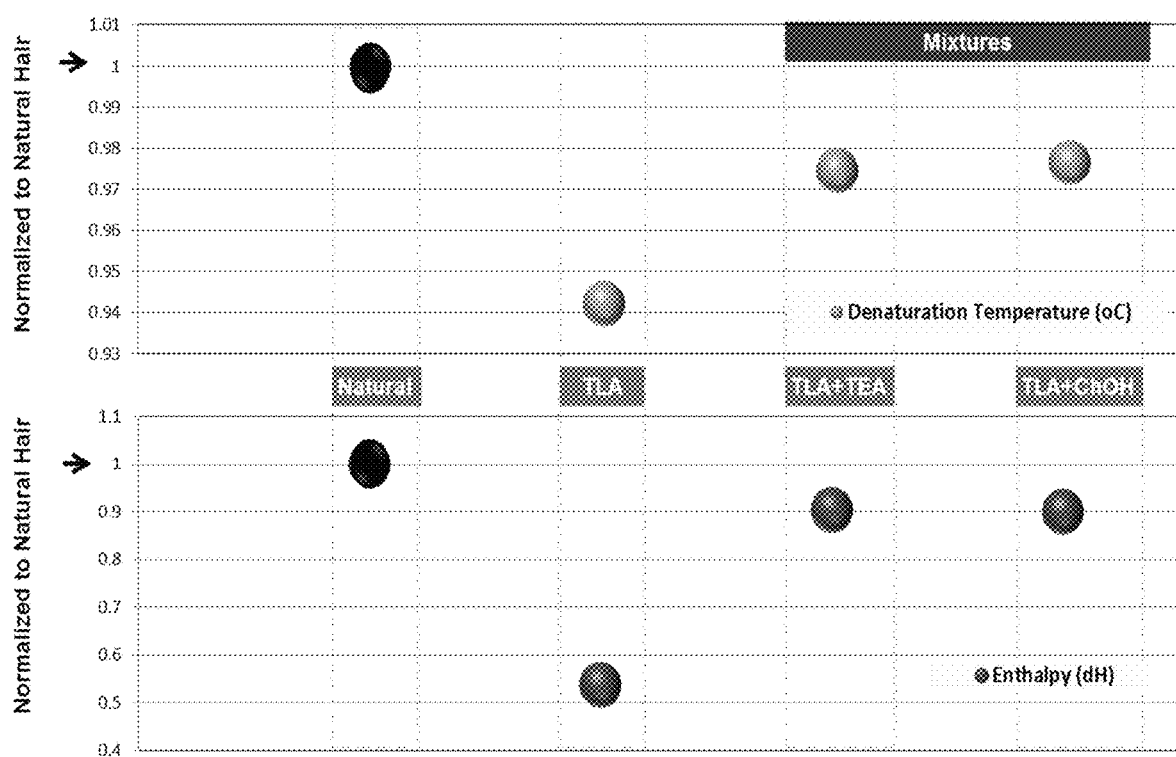
FIG. 4 is a graph showing the denaturation temperature and enthalpy of natural hair, hair treated with thiolactic acid, and hair treated with thiolactic acid-based ionic mixtures.

FIG. 3 shows the Young's Modulus, the break test results, and the break extension (%) for natural hair and compares it to the hair treated with thiolactic acid (TLA) alone, and hair treated with each of the ionic mixtures. FIG. 4 shows the denaturation temperature and enthalpy of natural hair and compares it to hair treated with thiolactic acid alone, and hair treated with each of the ionic mixtures.

The term "ionic liquid" has many definitions in the art, but is used herein to refer to salts (i.e., compositions comprising cations and anions) that are liquid at a temperature of at or below about 150° C. That is, at one or more temperature ranges or points at or below about 150° C. Further, the disclosed ionic liquids are materials composed of at least two different ions; each of which can independently and simultaneously introduce a specific characteristic to the composition not easily obtainable with traditional dissolution and formulation techniques. Thus, by providing different ions and ion combinations, the chemical and/or physical properties of the ionic liquid is often changed in ways not seen by simply mixing the components and/or preparing various crystalline salt forms. Examples of characteristics that can be controlled and/or changed with ionic liquids include, but are not limited to, melting, solubility control, and rate of dissolution. For instance, the ionic liquids of the instant disclosure often exhibit changed melting temperatures and changes in odor (reduction in odor). It is this multi-nature/functionality of the disclosed ionic liquids which allows one to fine-tune or design in very specific desired material properties."

The term "ionic mixture" refers to mixtures of components that form ionic interactions or ionic associations with each other but do not necessarily form an ionic bond. One difference between ionic liquids and ionic mixtures can be that with respect to ionic liquids, water and optionally salts are removed after the thiolactate anion and the one or more ammonium cationic compounds (ammonium cations) have formed an ionic association, thereby resulting in stronger ionic interactions between the thiolactate anion and ammonium cation. For ionic mixtures, further processing to remove water and optionally salts is not needed. Because ionic mixtures do not require formation of ionic bonds between thiocatatate anion and arnmmonium cation, a 1:1 ratio of these components is not needed. The stronger ionic bonding that occurs between thiolactate anion and ammonium cation in the ionic liquids results in the ionic liquids often exhibiting certain chemical and physical properties that are different than the physical and chemical properties observed by simply mixing thiolactic acid (and/or alkali earth and/or alkaline earth metal salts thereof) with one or more amine compounds and/or one or more ammonium cationic compounds and/or one or more salt thereof.

"Volatile", as used herein, means having a flash point of less than about 100° C.

"Non-volatile", as used herein, means having a flash point of greater than about 100° C.

The terms "a," "an," and "the" are understood to encompass the plural as well as the singular.

The expression "at least one" means "one or more" and vice versa, and thus includes individual components as well as mixtures/combinations.

As used herein, "cosmetically acceptable" means that the item in question is compatible with human keratin material and in particular human keratinous fibers, such as human hair.

The term "about" when referring to a value, is meant specifically that a measurement can be rounded to the value using a standard convention for rounding numbers. For example, "about 1.5" is 1.45 to 1.54. All values set forth herein can be modified with the term "about," if desired to impart the meaning above, or recited without the term, regardless of whether the term "about" is specifically set forth (or is absent) in conjunction with any particular value in the specification.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A method for shaping hair or altering the shape of hair or caring for the hair, the method comprising:
   (1) applying a hair care composition onto hair, wherein the hair care composition comprises:
      (a) an ionic liquid consisting of a thiolactate anion and one or more ammonium cationic compounds; and
      (b) an anhydrous cosmetically acceptable carrier;
   (2) optionally, brushing, combing, or smoothing the hair;
   (3) optionally, rinsing the hair;
   (4) heating the hair to temperature of at least 40° C., while optionally applying a smoothing or shaping action to the hair; and
   (5) optionally, rinsing the hair with water.

2. A method according to claim 1, wherein the method imparts to hair one or more of:
   straightening effects;
   (ii) manageability;
   (iii) frizz control;
   (iv) volume reduction or volume control;
   (v) styling effects;
   (vi) curling effects;
   (vii) texlaxing effects;
   (viii) relaxing effects;
   (ix) improvement or retention of curl definition;
   (x) humidity resistance; and/or
   (xi) improvement of the appearance of hair.

3. The method of claim 1, wherein the molar ratio of the thiolactate anion to the one or more ammonium cationic compounds in the ionic liquid is about 1:1.

4. The method of claim 1, wherein the thiolactate anion is derived from a compound selected from the group consisting of thiolactic acid, sodium thiolactic acid (sodium thiolactate), potassium thiolactic acid (potassium thiolactate), magnesium thiolactic acid (magnesium thiolactate), strontium thiolactic acid (strontium thiolactate), and mixtures thereof.

5. The method of claim 1, wherein the one or more ammonium cationic compounds are compounds of formula (I):

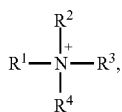

in which $R^1$, $R^2$, $R^3$ and $R^4$ are independently hydrogen, phenyl, benzyl, a saturated, branched or unbranched alkyl residue with a chain length of 1 to 30 carbon atoms, which may optionally be substituted with one or more hydroxyl groups, thiol groups, carboxylic groups, and/or aryl groups, wherein the alkyl residue with a chain length of 1 to 30 carbon atoms may be interrupted by one or more oxygen atoms, sulfur atoms, and/or NR groups, wherein R is hydrogen or a saturated, branched or unbranched alkyl residue with a chain length 1 to 6; and wherein at least one of $R^1$, $R^2$, $R^3$ and $R^4$ is not hydrogen.

6. The method of claim 1, wherein the one or more ammonium cationic compounds are derived from a compound selected from the group consisting of N,N,N-trimethylhydroxyethylammonium (choline) chloride, choline hydroxide, triethanolamine, monoethanolamine, and mixtures thereof.

7. The method of claim 1, wherein the hair care composition has a pH of about 3 to about 7.

8. A hair care composition comprising:
(a) an ionic liquid consisting of a thiolactate anion and one or more ammonium cationic compounds,
    wherein the thiolactate anion is derived from a compound selected from the group consisting of thiolactic acid, sodium thiolactic acid (sodium thiolactate), potassium thiolactic acid (potassium thiolactate), magnesium thiolactic acid (magnesium thiolactate), strontium thiolactic acid (strontium thiolactate), and mixtures thereof, and
    the one or more ammonium cationic compounds are derived from a compound selected from the group consisting of N,N,N-trimethylhydroxyethylammonium (choline) chloride, choline hydroxide, triethanolamine, monoethanolamine, and mixtures thereof;
(b) an anhydrous cosmetically acceptable carrier;
    wherein the composition has a pH of about 3 to about 7.

9. The hair care composition of claim 8, further comprising one or more dimethicone copolyols.

* * * * *